United States Patent
Walsh

(10) Patent No.: US 6,689,807 B1
(45) Date of Patent: Feb. 10, 2004

(54) HMG COA REDUCTASE INHIBITORS FOR PROMOTING ANGIOGENESIS

(75) Inventor: Kenneth Walsh, Carlisle, MA (US)

(73) Assignee: Caritas St. Elizabeth's Medical Center of Boston, Inc., Boston, MA (US)

(*) Notice: Subject to any disclaimer, the term of this patent is extended or adjusted under 35 U.S.C. 154(b) by 0 days.

(21) Appl. No.: 09/590,740

(22) Filed: Jun. 8, 2000

(51) Int. Cl.[7] .............................................. A01N 43/36
(52) U.S. Cl. ........................ 514/423; 514/510; 435/189
(58) Field of Search ................................ 514/423, 510; 435/189

(56) References Cited

U.S. PATENT DOCUMENTS

| | | | |
|---|---|---|---|
| 4,976,967 A | 12/1990 | McClelland et al. | 424/473 |
| 5,376,383 A | 12/1994 | Alberts et al. | 424/473 |
| 5,622,985 A | 4/1997 | Olukotun et al. | 514/423 |
| 5,674,893 A | 10/1997 | Behounek et al. | 514/451 |
| 5,902,805 A | 5/1999 | Breton et al. | 514/159 |
| 5,968,983 A | 10/1999 | Kaesemeyer | 514/564 |
| RE36,520 E | 1/2000 | Smith et al. | |
| 6,040,157 A | 3/2000 | Hu et al. | 435/69.4 |

FOREIGN PATENT DOCUMENTS

| | | |
|---|---|---|
| EP | WO 97/18303 | 5/1997 |
| WO | WO 99/18952 | 4/1999 |
| WO | WO 99/30704 | 6/1999 |
| WO | WO 00/20025 | 4/2000 |

OTHER PUBLICATIONS

Weis et al., "Statins Have Biphasic Effects On Angiogenesis" (2002) Circulation, 105(6), 739–745, Database CAPLUS, AN 2002:212119.*

Weis et al., "Statins Have Biphasic Effects On Angiogenesis" (2001a) Eur.Heart J., 22, Abstr. Suppl., 485, in Database DRUGU P, AN 2002–06077.*

Weis et al., "HMG–CoA Reductase Inhibition Has Biphasic Effects On Angiogenesis" (2001b) Circulation, 104, No. 17, Suppl., 124, in Database DRUGU P, AN 2002–09924.*

Kong et al., "HMG–CoA Reductase Inhibitors Interfere With VEGF Signaling In Human Endothelial Cells" (2000) Circulation, 102, No. 18, Suppl., 64, in Database DRUGU P, AN 2001–07231.*

Kong et al., "The Anti–Angiogenic Effects Of HMG CoA Reductase Inhibitors: A New Role For RhoA GTPase In The Regulation Of Angiogenesis" (1999) Circulation, 100, No. 18, Suppl., 39, Abst. 194.*

Carmen et al., "Double–Edged Role Of Statins In Angiogenesis Signaling" (2002) Circulation Research, 90 (6) 737–44, in Database IN–PROCESS, AN 2002201902.*

Anon., "Product news: Is angiogenesis another effect of the statins?" INPHARMA Oct. 12, 2000, in Database ADIS-NEWS, AN 2000:2406.*

Y. Kureishi, et al., "The HMH–CoA Reductase inhibitor simvastatin activates the protein kinase Akt and promotes angiogenesis in normocholesterolemic animals." *Nature Medicine* vol. 6: No. 8, pp 1004–1010 Sep. 2000.

International Search Report for PCT/US01/18175.

* cited by examiner

*Primary Examiner*—Jon P. Weber
(74) *Attorney, Agent, or Firm*—Edwards & Angell, LLP; David G. Conlin; Dianne M. Rees

(57) ABSTRACT

This invention relates to methods and compositions for the treatment of conditions associated with vascular insufficiency, and to methods and compositions for screening assays to select agents that are useful for this purpose. In particular the invention relates to HMG CoA reductase inhibitors and their use in promoting angiogenesis in vivo and in activating Akt in vascular endothelial cells in vitro and in vivo.

31 Claims, 9 Drawing Sheets

SEQUENCE LISTING

```
<160> NUMBER OF SEQ ID NOS:  6

<210> SEQ ID NO 1
<211> LENGTH: 2610
<212> TYPE: DNA
<213> ORGANISM: Homo sapiens

<400> SEQUENCE: 1
atcctgggac agggcacagg gccatctgtc accagggct tagggaaggc cgagccagcc      60
tgggtcaaag aagtcaaagg ggctgcctgg aggaggcagc ctgtcagctg gtgcatcaga     120
ggctgtggcc aggccagctg ggctcgggga gcgccagcct gagaggagcg cgtgagcgtc     180
gcgggagcct cgggcaccat gagcgacgtg gctattgtga aggagggttg gctgcacaaa    240 cgagggagt acatcaagac ctggcggcca cgctacttcc tcctcaagaa tgatggcacc     300
ttcattggct acaaggagcg gccgcaggat gtggaccaac gtgaggctcc cctcaacaac    360
```

-continued

```
ttctctgtgg cgcagtgcca gctgatgaag acggagcggc cccggcccaa caccttcatc    420
atccgctgcc tgcagtggac cactgtcatc gaacgcacct tccatgtgga gactcctgag    480
gagcgggagg agtggacaac cgccatccag actgtggctg acggcctcaa gaagcaggag    540
gaggaggaga tggacttccg gtcgggctca cccagtgaca actcaggggc tgaagagatg    600
gaggtgtccc tggccaagcc caagcaccgc gtgaccatga acgagtttga gtacctgaag    660
ctgctgggca agggcacttt cggcaaggtg atcctggtga aggagaaggc cacaggccgc    720
tactacgcca tgaagatcct caagaaggaa gtcatcgtgg ccaaggacga ggtggcccac    780
acactcaccg agaaccgcgt cctgcagaac tccaggcacc ccttcctcac agccctgaag    840 tactcttttcc agacccacga ccgcctctgc tttgtcatgg agtacgccaa cggggcgag    900 ctgttcttcc acctgtcccg ggaacgtgtg ttctccgagg accgggcccg cttctatggc   960
gctgagattg tgtcagccct ggactacctg cactcggaga gaacgtggt gtaccgggac    1020 ctcaagctgg agaacctcat gctggacaag gacgggcaca ttaagatcac agacttcggg   1080
ctgtgcaagg aggggatcaa ggacggtgcc accatgaaga ccttttgcgg cacacctgag   1140
tacctggccc ccgaggtgct ggaggacaat gactacggcc gtgcagtgga ctggtggggg   1200
ctgggcgtgt tcatgtacga gatgatgtgc ggtcgcctgc ccttctacaa ccaggaccat   1260
gagaagcttt tgagctcat cctcatggag gagatccgct cccgcgcac gcttggtccc    1320 gaggccaagt ccttgctttc agggctgctc aagaaggacc ccaagcagag gcttggcggg   1380
ggctccgagg acgccaagga gatcatgcag catcgcttct tgccggtat cgtgtggcag    1440 cacgtgtacg agaagaagct cagcccaccc ttcaagcccc aggtcacgtc ggagactgac   1500
accaggtatt tgatgagga gttcacggcc cagatgatca ccatcacacc cctgaccaa    1560 gatgacagca tggagtgtgt ggacagcgag cgcaggcccc acttccccca gttctcctac   1620
tcggccagca gcacggcctg aggcggcggt ggactgcgct ggacgatagc ttggagggat   1680
ggagaggcgg cctcgtgcca tgatctgtat ttaatggttt ttatttctcg ggtgcatttg   1740
agagaagcca cgctgtcctc tcgagcccag atggaaagac gtttttgtgc tgtgggcagc   1800
accctccccc gcagcgggt agggaagaaa actatcctgc gggttttaat ttatttcatc   1860
cagtttgttc tccgggtgtg gcctcagccc tcagaacaat ccgattcacg tagggaaatg   1920
ttaaggactt ctacagctat gcgcaatgtg gcattggggg gccgggcagg tcctgcccat   1980
gtgtcccctc actctgtcag ccagccgccc tgggctgtct gtcaccagct atctgtcatc   2040 tctctgggc cctgggcctc agttcaacct ggtggcacca gatgcaacct cactatggta   2100
tgctggccag caccctctcc tgggggtggc aggcacacag cagcccccca gcactaaggc   2160
cgtgtctctg aggacgtcat cggaggctgg gccctggga tgggaccagg gatgggggat    2220
gggccagggt tacccagtg ggacagagga gcaaggttta aatttgttat tgtgtattat   2280
gttgttcaaa tgcatttgg gggttttaa tctttgtgac aggaaagccc tcccccttcc    2340
ccttctgtgt cacagttctt ggtgactgtc ccaccgagc ctccccctca gatgatctct    2400
ccacggtagc acttgacctt ttcgacgctt aacctttccg ctgtcgcccc aggccctccc   2460
tgactccctg tggggtggc catccctggg ccctccacg cctcctggcc agacgctgcc    2520
gctgccgctg caccacggcg ttttttaca acattcaact ttagtatttt tactattata   2580
atataatatg gaaccttccc tccaaattct                                   2610
```

<210> SEQ ID NO 2

```
<211> LENGTH: 480
<212> TYPE: PRT
<213> ORGANISM: Homo sapiens

<400> SEQUENCE: 2

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Lys Asn Asp
            20                  25                  30

Gly Thr Phe Ile Gly Tyr Lys Glu Arg Pro Gln Asp Val Asp Gln Arg
            35                  40                  45

Glu Ala Pro Leu Asn Asn Phe Ser Val Ala Gln Cys Gln Leu Met Lys
        50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
```

```
                385                 390                 395                 400
            Glu Ile Met Gln His Arg Phe Phe Ala Gly Ile Val Trp Gln His Val
                        405                 410                 415
            Tyr Glu Lys Lys Leu Ser Pro Pro Phe Lys Pro Gln Val Thr Ser Glu
                        420                 425                 430
            Thr Asp Thr Arg Tyr Phe Asp Glu Glu Phe Thr Ala Gln Met Ile Thr
                        435                 440                 445
            Ile Thr Pro Pro Asp Gln Asp Asp Ser Met Glu Cys Val Asp Ser Glu
                        450                 455                 460
            Arg Arg Pro His Phe Pro Gln Phe Ser Tyr Ser Ala Ser Ser Thr Ala
            465                 470                 475                 480

<210> SEQ ID NO 3
<211> LENGTH: 1254
<212> TYPE: DNA
<213> ORGANISM: Homo sapiens

<400> SEQUENCE: 3
atgaagacgg agcggccccg gcccaacacc ttcatcatcc gctgcctgca gtggaccact      60
gtcatcgaac gcaccttcca tgtggagact cctgaggagc gggaggagtg gacaaccgcc     120
atccagactg tggccgacgg cctcaagaag caggaggagg aggagatgga cttccggtcg     180
ggctcaccca gcgacaactc aggggccgaa gagatggagg tgtccctggc caagcccaag     240
caccgcgtga ccatgaacga gtttgagtac ctgaagctgc tgggcaaggg cacttttcggc    300
aaggtgatcc tggtgaagga gaaggccaca gcgtactacg ccatgaagat cctcaagaag    360
gaagtcatcg tggccaagga cgaggtggcc acacactca ccgagaaccg cgtccagcag     420
aactccaggc acccctctcct cactcgcctg aagtactctt tccagaccca cgaccgcctc    480
tgctttgtca tggagtacgc caacgggggc gagctgttct tccacctgtc ccgggagcgt    540
gtgttcgccg aggaccgggc ccgcttctat ggcgctgaga ttgtgtcagc cctggactac    600
ctgcactcgg agaagaacgt ggtgtaccgg gacctcaagc tggagaacct catgctggac    660
aaggacgggc acattaagat cacagacttc gggctgtgca aggaggggat caaggacggt    720
gccaccatga gacccttttg cggcacacct gagtacctgg cccccgaggt gctggaggac    780
aatgactacg gccgtgcagt ggactggtgg gggctgggcg tggtcatgta cgagatgatg    840
tgcggtcgcc tgcccttcta caaccaggac atgagaagc tttttgagct catcctcatg    900
gaggagatcc gcttcccgcg cacgcttggt cccgaggcca agtccttgct ttcagggctg    960
ctcaagaagg accccaagca gaggcttggc gggggctccg aggacgccaa ggagatcatg   1020
cagcatcgct tctttaccgg tatcgtgtgg cagcacgtgt acgagaagaa gctcagccca   1080
cccttcaagc cccaggtcac gtcggagact gacaccaggt attttgatga ggagttcacg   1140
gcccagatga tcaccatcac accacctgac caagatgaca gcatggagtg tgtggacagc   1200
gagcgcaggc cccacttccc ccagttctcc tactcgccca gcgcgacggc ctga         1254

<210> SEQ ID NO 4
<211> LENGTH: 417
<212> TYPE: PRT
<213> ORGANISM: Homo sapiens

<400> SEQUENCE: 4

Met Lys Thr Glu Arg Pro Arg Pro Asn Thr Phe Ile Ile Arg Cys Leu
1               5                   10                  15

Gln Trp Thr Thr Val Ile Glu Arg Thr Phe His Val Glu Thr Pro Glu
```

-continued

```
                  20                      25                      30
Glu Arg Glu Glu Trp Thr Thr Ala Ile Gln Thr Val Ala Asp Gly Leu
                35                      40                      45

Lys Lys Gln Glu Glu Glu Met Asp Phe Arg Ser Gly Ser Pro Ser
 50                      55                      60

Asp Asn Ser Gly Ala Glu Glu Met Glu Val Ser Leu Ala Lys Pro Lys
 65                      70                      75                      80

His Arg Val Thr Met Asn Glu Phe Glu Tyr Leu Lys Leu Leu Gly Lys
                        85                      90                      95

Gly Thr Phe Gly Lys Val Ile Leu Val Lys Glu Lys Ala Thr Ala Tyr
                    100                     105                     110

Tyr Ala Met Lys Ile Leu Lys Lys Glu Val Ile Val Ala Lys Asp Glu
                115                     120                     125

Val Ala His Thr Leu Thr Glu Asn Arg Val Gln Gln Asn Ser Arg His
            130                     135                     140

Pro Phe Leu Thr Arg Leu Lys Tyr Ser Phe Gln Thr His Asp Arg Leu
145                     150                     155                     160

Cys Phe Val Met Glu Tyr Ala Asn Gly Gly Glu Leu Phe Phe His Leu
                    165                     170                     175

Ser Arg Glu Arg Val Phe Ala Glu Asp Arg Ala Arg Phe Tyr Gly Ala
                180                     185                     190

Glu Ile Val Ser Ala Leu Asp Tyr Leu His Ser Glu Lys Asn Val Val
            195                     200                     205

Tyr Arg Asp Leu Lys Leu Glu Asn Leu Met Leu Asp Lys Asp Gly His
        210                     215                     220

Ile Lys Ile Thr Asp Phe Gly Leu Cys Lys Glu Gly Ile Lys Asp Gly
225                     230                     235                     240

Ala Thr Met Lys Thr Phe Cys Gly Thr Pro Glu Tyr Leu Ala Pro Glu
                    245                     250                     255

Val Leu Glu Asp Asn Asp Tyr Gly Arg Ala Val Asp Trp Trp Gly Leu
                260                     265                     270

Gly Val Val Met Tyr Glu Met Met Cys Gly Arg Leu Pro Phe Tyr Asn
            275                     280                     285

Gln Asp His Glu Lys Leu Phe Glu Leu Ile Leu Met Glu Glu Ile Arg
        290                     295                     300

Phe Pro Arg Thr Leu Gly Pro Glu Ala Lys Ser Leu Leu Ser Gly Leu
305                     310                     315                     320

Leu Lys Lys Asp Pro Lys Gln Arg Leu Gly Gly Ser Glu Asp Ala
                    325                     330                     335

Lys Glu Ile Met Gln His Arg Phe Phe Thr Gly Ile Val Trp Gln His
                340                     345                     350

Val Tyr Glu Lys Lys Leu Ser Pro Pro Phe Lys Pro Gln Val Thr Ser
            355                     360                     365

Glu Thr Asp Thr Arg Tyr Phe Asp Glu Glu Phe Thr Ala Gln Met Ile
        370                     375                     380

Thr Ile Thr Pro Pro Asp Gln Asp Asp Ser Met Glu Cys Val Asp Ser
385                     390                     395                     400

Glu Arg Arg Pro His Phe Pro Gln Phe Ser Tyr Ser Pro Ser Ala Thr
                    405                     410                     415

Ala

<210> SEQ ID NO 5
<211> LENGTH: 2626
```

-continued

<212> TYPE: DNA
<213> ORGANISM: Mus musculus

<400> SEQUENCE: 5

```
ccgggaccag cggacggacc gagcagcgtc ctgcggccgg caccgcggcg gcccagatcc      60
ggccagcagc gcgcgcccgg acgccgctgc cttcagccgg ccccgcccag cgcccgcccg     120
cgggatgcgg agcggcgggc gcccgaggcc gcggcccggc taggcccagt cgcccgcacg     180
cggcggcccg acgctgcggc caggccggct gggctcagcc taccgagaag agactctgat     240
catcatccct gggttacccc tgtctctggg gccacggat accatgaacg acgtagccat      300
tgtgaaggag ggctggctgc acaaacgagg ggaatatatt aaaacctggc ggccacgcta     360
cttcctcctc aagaacgatg gcacctttat tggctacaag gaacgcctc aggatgtgga      420
tcagcgagag tccccactca caacttctc agtggcacaa tgccagctga tgaagacaga      480
gcggccaagg cccaacacct ttatcatccg ctgcctgcag tggaccacag tcattgagcg     540
caccttccat gtggaaacgc ctgaggagcg ggaagaatgg gccaccgcca ttcagactgt     600
ggccgatgga ctcaagaggc aggaagaaga gacgatggga ttccgatcag gctcacccag     660
tgacaactca ggggctgaag agatggaggt gtccctggcc aagcccaagc accgtgtgac     720
catgaacgag tttgagtacc tgaaactact gggcaagggc acctttggga agtgattct      780
ggtgaaagag aaggccacag gccgctacta tgccatgaag atcctcaaga aggaggtcat     840
cgtcgccaag gatgaggttg cccacacgct tactgagaac cgtgtcctgc agaactctag     900
gcatcccttc cttacggccc tcaagtactc attccagacc cacgaccgcc tctgctttgt     960
catggagtat gccaacgggg gcgagctctt cttccacctg tctcgagagc gcgtgttctc    1020
cgaggaccgg gcccgcttct atggtgcgga gattgtgtct gccctggact acttgcactc    1080
cgagaagaac gtggtgtacc gggacctgaa gctggagaac ctcatgctgg acaaggacgg    1140
gcacatcaag ataacggact cgggctgtg caaggagggg atcaaggatg gtgccactat     1200
gaagacattc tgcggaacgc cggagtacct ggcccctgag gtgctggagg acaacgacta    1260
cggccgtgca gtggactggt gggggctggg cgtggtcatg tatgagatga tgtgtggccg    1320
cctgcccttc tacaaccagg accacgagaa gctgttcgag ctgatcctca tggaggagat    1380
ccgcttcccg cgcacactcg gccctgaggc caagtccctg ctctccgggc tgctcaagaa    1440
ggaccctaca cagaggctcg gtgggggctc tgaggatgcc aaggagatca tgcagcaccg    1500
gttctttgcc aacatcgtgt ggcaggatgt gtatgagaag aagctgagcc cacctttcaa    1560
gccccaggtc acctctgaga ctgacaccag gtatttcgat gaggagttca cagctcagat    1620
gatcaccatc acgcgcctg atcaagatga cagcatggag tgtgtggaca gtgagcggag    1680
gccgcacttc ccccagttct cctactcagc cagtggcaca gcctgaggcc tggggcagcg    1740
gctggcagct ccacgctcct ctgcattgcc gagtccagaa gccccgcatg gatcatctga    1800
acctgatgtt tgtttctcg gatgcgctgg ggaggaacct tgccagcctc aggaccagg     1860
ggaggatgtt tctactgtgg gcagcagcct acctcccagc caggtcagga ggaaaactat    1920
cctggggttt ttcttaattt atttcatcca gtttgagacc acacatgtgg cctcagtgcc    1980
cagaacaatt agattcatgt agaaaactat taaggactga cgcgaccatg tgcaatgtgg    2040
gctcatgggt ctgggtgggt cccgtcactg cccccattgg cctgtccacc ctggccgcca    2100
cctgtctcta gggtccaggg ccaaagtcca gcaagaaggc accagaagca cctccctgtg    2160
gtatgctaac tggccctctc cctctgggcg gggagaggtc acagctgctt cagccctagg    2220
```

-continued

```
gctggatggg atggccaggg ctcaagtgag gttgacagag gaacaagaat ccagtttgtt    2280
gctgtgtccc atgctgttca gagacattta ggggatttta atcttggtga caggagagcc    2340
cctgccctcc cgctcctgcg tggtggctct tagcgggtac cctgggagcg cctgcctcac    2400
gtgagccctc tcctagcact tgtccttta gatgctttcc ctctcccgct gtccgtcacc     2460
ctggcctgtc ccctcccgcc agacgctggc cattgctgca ccatgtcgtt ttttacaaca    2520
ttcagcttca gcatttttac tattataata agaaactgtc cctccaaatt caataaaaat   2580
tgcttttcaa gcttgaaaaa aaaaaaaaaa aaaaaaaaa aaaaaa                    2626
```

<210> SEQ ID NO 6
<211> LENGTH: 480
<212> TYPE: PRT
<213> ORGANISM: Mus musculus

<400> SEQUENCE: 6

```
Met Asn Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
         35                  40                  45

Glu Ser Pro Leu Asn Asn Phe Ser Val Ala Gln Cys Gln Leu Met Lys
     50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Ala Thr Ala Ile Gln Thr Val Ala Asp Gly Leu Lys Arg
            100                 105                 110

Gln Glu Glu Glu Thr Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300
```

```
-continued

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Thr Gln Arg Leu Gly Gly Gly Ser Glu Asp Ala Lys
385                 390                 395                 400

Glu Ile Met Gln His Arg Phe Phe Ala Asn Ile Val Trp Gln Asp Val
            405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480
```

HMG COA REDUCTASE INHIBITORS FOR PROMOTING ANGIOGENESIS

FIELD OF THE INVENTION

Figure 1A:
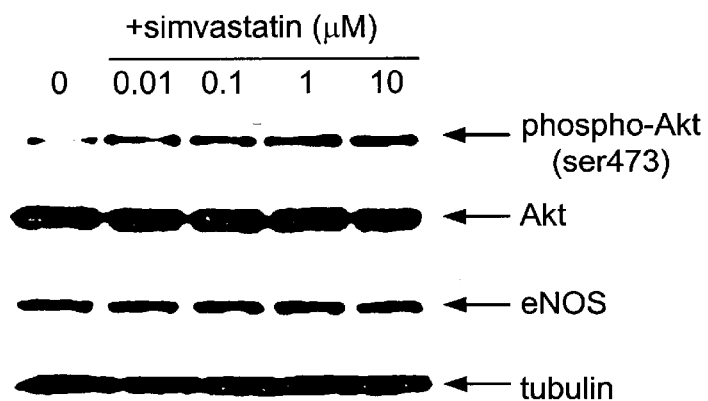

This invention relates to methods and compositions for the treatment of conditions associated with vascular insufficiency, and to methods and compositions for screening assays to select agents that are useful for this purpose. In particular, the invention relates to HMG CoA reductase inhibitors and their use in promoting angiogenesis in vivo and in activating Akt in vascular endothelial cells in vitro and in vivo.

BACKGROUND OF THE INVENTION

Akt Protein Kinases

Akt (c-Akt) is a proto-oncogene encoding a serine-threonine kinase (Testa, J. R. and Bellacosa, A., *Leukemia Res.*, 1997, 21:1027–1031). It is the cellular homolog of the viral oncoprotein v-Akt, and is related to protein kinase-C (PKC) within the catalytic domain. However, c-Akt differs from the PKC family members by the presence of a pleckstrin homology (PH) domain at its N-terminus that is involved in the regulation of the activity of the enzyme by growth factors and intracellular signaling molecules. Various extracellular stimuli reportedly activate Akt through the phosphoinositide 3-kinase (PI 3-kinase) pathway (Datta, K. et al., *J. Biol. Chem.*, 1996, 271:30835–30839; Franke, T. F., et al., *Cell*, 1995, 81:727–736; King, W. G. et al., *Mol. Cell. Biol.*, 1997, 17:4406–4418). The lipid products of the PI 3-kinase reaction reportedly may activate Akt either by binding to the Akt pleckstrin homology (PH) domain (Franke, T. F. et al., 1997, Cell, 88:435:437), or by activating a protein kinase that phosphorylates Akt (Kohn, A. D., et al., *J. Biol. Chem.*, 1996, 271:21920–21926; Stokoe et al., *Science*, 1997, 277:567–570). Activation of Akt reportedly inhibits apoptosis induced by growth factor withdrawal or irradiation in neural cells, fibroblasts, and lymphocytes (Franke, T. F., et al., *Science*, 1997, 275:665–668; Hemmings, *Science*, 1997, 275:628–630). Recently, it has been reported that Akt phosphorylates the pro-apoptotic protein Bad leading to Bad inactivation and cell survival (Datta, K., et al., *Cell*, 1997, 91:231–241; Peso, L., et al., *Science*, 1997, 278:687–689).

Despite the foregoing speculation, the precise mechanism underlying Akt activation in vivo has yet to be elucidated. Accordingly, a need still exists to identify the precise mechanism underlying Akt activation in vivo and to use such knowledge to develop methods and compositions for treating conditions that are amenable to treatment by Akt activation in vivo, as well as to develop screening assays that are useful for identifying agents which activate Akt in vivo and in vitro.

HMG-CoA Reductase Inhibitors

HMG-CoA (3-hydroxy-3-methylglutaryl-coenzyme A) reductase is the enzyme which catalyzes the rate limiting step of cholesterol biosynthesis. HMG-CoA reductase inhibitors, also known as statins, are molecules which inhibit the enzymatic activity of HMG-CoA reductase and have been used to treat patients suffering from hypercholesterolemia. The first such inhibitor (compactin or Mevastatin) was isolated in 1976 (Endo, A. et al., *F.E. B.S. Lett.*, 72: 323–326, 1976) and since then many other natural and chemically modified versions of Mevastatin have been identified and developed for clinical use, including Lovastatin, and Simvastatin.

Recent studies have shown that, in addition to treatment of hyperlipidemia, HMG-CoA reductase inhibitors are useful in the treatment of acne and/or skin aging (see, e.g. Breton, L. et al., U.S. Pat. No. 5,902,805); can increase nitric oxide (NO)-mediated vasodilation and blood vessel relaxation (see e.g., Liao, J. K. et al., WO 99/18952); and can help prevent a second or additional myocardial infarction (see, e.g., Behounek, B. D. et al., U.S. Pat. No. 5,674,893; Olukotun, A. Y. et al., U.S. Pat. No. 5,622,985).

Additonally, several studies have shown that HMG-CoA reductase inhibitors have anti-angiogenic activity. Feleszko, W. et al., *Int. J. Cancer*, 81: 560–567 (1999) reported that treatment of a mouse model of tumor-cell induced angiogenesis with a combination of TNF-$\alpha$ and lovastatin produced a significant inhibition of tumor-induced blood-vessel formation whereas treatment with either TNF-$\alpha$ or lovastatin alone showed no angiostatic effects. Jones, M. K. et al., *Am. J. Physiol.*, 276: G1345–GI1355 (1999) reported that mevastatin, an inhibitor of Ras activation, completely blocked the induction of VEGF (a potent angiogenic factor) expression in cultured primary endothelial cells. Kong, D. et al., *Circulation*, 100(18): I-39, Abstract #194 (1999) reported that simvastatin exerted potent anti-angiogenic effects independent of its cholesterol lowering effects.

SUMMARY OF THE INVENTION

To understand the mechanism by which angiogenic agents such as VEGF promote new blood vessel formation (angiogenesis), we have analyzed the signaling pathways downstream from the growth factor. In particular, we have analyzed Akt signaling in endothelial cells. Akt (also known as Protein Kinase-B, PKB) inhibits apoptotic cell-death and, in particular, inhibits apoptotic cell-death of cardiomyocytes, skeletal myocytes and/or vascular endothelial cells. (See, e.g., U.S. Ser. No. 9/922,633, entitled, "Akt Compositions for Enhancing Survival of Cells", PCT Application No. PCT/US99/22633, published as WO 00/20025). In the course of analyzing Akt signaling events in an animal model of ischemia, we have surprisingly discovered that activation of Akt signaling in endothelial cells is sufficient to promote angiogenesis. We also have discovered that HMG CoA reductase inhibitors such as simvastatin are potent activators of Akt. In view of these discoveries, we believe that simvastatin and other HMG CoA reductase inhibitors can be used to promote angiogenesis in tissues, and that such inhibitors are useful for treating conditions in which new blood vessel growth is desirable to treat the condition. These discoveries were highly unexpected in view of previous research indicating that HMG CoA reductase inhibitors had angiostatic activity.

According to one aspect of the invention, a method for promoting angiogenesis in a tissue of a subject in need of such treatment is provided. The method involves administering to the subject, an HMG CoA reductase inhibitor in an amount effective to promote angiogenesis in the tissue, preferably in situations where the subject is not otherwise in need of administration of an HMG CoA reductase inhibitor. According to this aspect, the subject may or may not be hyperlipidemic and/or hypercholesterolemic. In certain embodiments, the method further includes the step of detecting angiogenesis in the tissue.

Conditions that can be treated in accordance with this method of the invention (administration by any route, preferably oral administration) are conditions characterized by insufficient vascularization (or predisposition thereto) of the affected tissue, i.e., conditions in which neovascularization (rather than increases in nitric oxide (NO)-mediated vasodilation) is needed to achieve sufficient vascularization in the affected tissue, and that are selected from the following group of conditions: (1) diabetic ulcers, (2) gangrene, (3) surgical or other wounds requiring neovascularization to facilitate healing; (4) Buerger's syndrome; (5) hypertension; (6) ischemic diseases including, for example, cerebrovascular ischemia, renal ischemia, pulmonary ischemia, limb ischemia, ischemic cardiomyopathy, myocardial ischemia, ischemia of tissues such as, for example, muscle, brain, kidney and lung; and other conditions characterized by a reduction in microvasculature. The preferred method of treatment further includes the step of detecting angiogenesis in the affected tissue following treatment. Exemplary tissues in which angiogenesis can be promoted and, optionally, detected in accordance with this method of the invention include: hypertension; ulcers (e.g., diabetic ulcers); surgical wounds; ischemic tissue, i.e., a tissue having a deficiency in blood as the result of an ischemic disease including, for example, muscle, brain, kidney and lung; ischemic diseases including, for example, cerebrovascular ischemia, renal ischemia, pulmonary ischemia, limb ischemia, ischemic cardiomyopathy and myocardial ischemia. In the preferred embodiments, the HMG CoA reductase inhibitor is a statin molecule (see description below). More preferably, the statin molecule(s) is orally administered.

According to yet another aspect of the invention, a method for promoting angiogenesis in a tissue of a subject is provided. The method involves locally administering to the tissue, an HMG CoA reductase inhibitor in an amount effective to promote angiogenesis in the tissue. Preferably, the subject is not otherwise in need of administration (particularly, local administration) of an HMG CoA reductase inhibitor. According to certain embodiments, the subject is hyperlipidemic and/or hypercholesterolemic. According to yet other embodiments, the subject is nonhyperlipidemic and/or nonhypercholesterolemic.

Conditions that can be treated in accordance with this method of the invention (locally administering the therapeutic agent to the tissue) are conditions characterized by insufficient vascularization of the affected tissue, i.e., conditions in which neovascularization, rather than nitric oxide mediated vasodilation, is desirable to achieve sufficient vascularization in the affected tissue. Exemplary conditions that can be treated in accordance with the methods of the invention include: (1) severe occlusive and/or obstructive vascular disease, such as (a) peripheral vascular disease (particularly, diabetic peripheral vascular disease), (b) myocardial ischemia /myocardial infarction, (c) coronary artery disease, (d) cerebral vascular disease, (e) visceral vascular disease; and (2) surgical or other wounds requiring neovascularization to facilitate healing. The preferred method of treatment further includes the step of detecting angiogenesis in the affected tissue following treatment. Exemplary tissues to which the HMG CoA reductase inhibitor can be administered in accordance with the methods of the invention to promote angiogenesis therein include cardiac tissue, ulcers (e.g., diabetic ulcers), surgical wounds, neuronal tissue (e.g., tissue damaged incident to ischemia of the brain), and other tissue damaged as a result of severe occlusive and/or obstructive vascular disease or injury.

An HMG CoA reductase inhibitor is a term of art which refers to a molecule which inhibits the enzymatic activity of the enzyme, HMG-CoA (3-hydroxy-3-methylglutaryl-coenzyme A) reductase. As used herein, the HMG CoA reductase inhibitors that are useful in accordance with the methods of the invention satisfy the conventional meaning of this phrase and are capable of activating Akt signaling in vascular endothelial cells. As used herein, "activating Akt signaling" refers to inducing a change in the Akt polypeptide that is sufficient to promote angiogenesis when the activation occurs in vivo. In general, the change that is induced is phosphorylation of the Akt polypeptide, typically at Ser 473 and/or Thr 308. Exemplary HMG CoA reductase inhibitors are provided in the detailed description of this invention and in the references and/or patent documents identified therein. The preferred HMG CoA reductase inhibitors that are useful in accordance with the methods and compositions of the invention are statin molecules. These include: Lovastatin (Mevacor), Pravastatin (Pravachol), Simvastatin (Zocor), Fluvastatin (Lescol), Atorvastatin (Lipitor), or Cerivastatin (Baycol), provided that when the statin molecule is an inhibitor of HMG CoA, it is processed into the corresponding lactone form prior to local administration. Also provided are screening assays for selecting novel inhibitors which are capable of activating Akt signaling in vascular endothelial cells.

The preferred methods of treatment for this aspect of the invention involve locally administering the HMG CoA reductase to the tissue of a subject in an amount effective to promote angiogenesis in the tissue. In certain embodiments, locally administering involves inserting a stent containing the HMG CoA reductase inhibitor into the tissue. Alternatively, locally administering involves administering to the subject a pharmaceutical composition containing an HMG CoA reductase inhibitor and a pharmaceutically acceptable carrier. In certain preferred embodiments, the pharmaceutical composition is suitable for topical application or internal applications and can be formulated as a salve, a gel or a patch. Preferably, the pharmaceutical composition is a controlled release matrix and, more preferably, the composition is formulated to release the HMG CoA reductase inhibitor substantially continuously for a period of at least one day (i.e. a sustained release formulation).

According to yet another aspect of the invention, a method for activating an Akt polypeptide is provided. The method involves contacting a cell containing an Akt polypeptide with an HMG CoA reductase inhibitor in vitro under conditions wherein the HMG CoA reductase inhibitor (preferably a statin molecule as described herein) activates the Akt polypeptide. By "activate" it is meant that the HMG CoA reductase inhibitor facilitates the transformation of the Akt polypeptide from an inactive to an active form. This transition can be determined by detecting various parameters, e.g., degree of Akt polypeptide phosphorylation, degree of phosphorylation of an Akt substrate molecule (e.g. Bad, histone H2B, eNOS, etc., or fragments thereof), or other downstream signaling events, including for example a change in the rate of protein degradation, a change in the level of mRNA transcription, a change in the level of protein translation, reduction of apoptosis, induction of angiogenesis, etc. Although not wishing to be bound to any particular theory or mechanism, it is believed that HMG CoA reductase inhibitors facilitate the phosphorylation of the Akt polypeptide (e.g., at Ser 473 and/or Thr 308) which mediates further signaling events that result in angiogenesis in vivo. Thus, in particularly preferred embodiments such as those methods useful as screening assays, the Akt polypeptide that is useful in this aspect of the invention is an Akt polypeptide that is expressed by a vascular endothelial cell. Exemplary Akt polypeptides are described in U.S. Ser. No.

9/922,633, entitled, "Akt Compositions for Enhancing Survival of Cells", PCT Application No. PCT/US99/22633, published as WO 00/20025. The preferred Akt polypeptide has SEQ ID NO. 1. Exemplary conditions for performing this aspect of the invention are provided in the Examples.

According to still another aspect of the invention, a method for promoting angiogenesis by activating an Akt molecule is provided. The method involves contacting a cell containing an Akt polypeptide with an HMG CoA reductase inhibitor in vitro under conditions wherein the HMG CoA reductase inhibitor (preferably a statin molecule as described herein) activates the Akt polypeptide. While not wishing to be bound by theory, it is believed that activation of Akt allows Akt molecules to initiate signalling events which lead to promotion of angiogenesis. In particularly preferred embodiments such as those methods useful as screening assays, the Akt polypeptide that is useful in this aspect of the invention is an Akt polypeptide that is expressed by a vascular endothelial cell. Exemplary Akt polypeptides are described in U.S. Ser. No. 9/922,633, entitled, "Akt Compositions for Enhancing Survival of Cells", PCT Application No. PCT/US99/22633, published as WO 00/20025. The preferred Akt polypeptide has SEQ ID NO. 1.

According to yet another aspect of the invention, a screening method to identify putative HMG CoA reductase inhibitors that activate an Akt polypeptide is provided. The method involves performing an Akt polypeptide activation (e.g., phosphorylation) assay in the presence and absence of a putative HMG CoA reductase inhibitor; and determining the level of Akt polypeptide activation in the presence and absence of the putative inhibitor, wherein an increase in the level of Akt polypeptide activation in the presence of the putative inhibitor relative to the level of Akt polypeptide activation in the absence of the putative inhibitor indicates that the putative inhibitor is an HMG CoA reductase inhibitor as used herein.

According to still another aspect of the invention, a method for treating a wound (e.g., a surgical wound) is provided. The method involves contacting the wound with a sufficient amount of an HMG CoA reductase inhibitor under conditions wherein the HMG CoA reductase inhibitor causes neovasculatization and enhances healing of the wound. In certain embodiments, contacting the wound involves locally administering the HMG CoA reductase inhibitor to the wound. For example, the HMG CoA reductase inhibitor can be contained in a pharmaceutical composition that is formulated for local administration to a wound or to a tissue in need of neovascularization in a subject.

According to a further aspect of the invention, a pharmaceutical composition is provided. The composition comprises an HMG CoA reductase inhibitor (preferably, a statin molecule as described herein); and a pharmaceutically acceptable carrier suitable for local delivery to a wound or a tissue in need of neovascularization in a subject. In certain embodiments, the composition is suitable for non-oral, preferably topical or intramuscular applications. In these and other embodiments, the composition optionally is formulated as a salve, a gel, or a patch. In particularly preferred embodiments, the composition is a controlled release matrix and, more preferably, the composition is formulated to release the HMG CoA reductase inhibitor substantially continuously for a period of at least a day. Methods for preparing such pharmaceutical compositions are also provided.

According to yet another aspect of the invention, the pharmaceutical composition may additionally comprises an angiogenic growth factor. Preferred angiogenic growth factors include, for example, acidic and basic fibroblast growth factors, vascular endothelial growth factor, epidermal growth factor, transforming growth factor α and β, platelet-derived endothelial cell growth factor, platelet-derived growth factor, tumor necrosis factor a, hepatocyte growth factor, insulin like growth factor, etc. In a particular embodiment the pharmaceutical composition contains an Akt protein, preferably in a constitutively active form. According to still another aspect of the invention, the pharmaceutical composition may comprise a nucleic acid encoding for an angiogenic growth factor or an Akt protein.

In a particularly preferred embodiment, coadministration of an HMG CoA reductase inhibitor with an Akt molecule produces a syngeristic effect wherein the resultant angiogenesis observed with the coadministration is greater than the angiogenesis that would be expected from the additive effects when either the HMG CoA reductase inhibitor or the Akt molecule is administered alone.

Pharmaceutical compositions comprising angiogenic growth factor proteins, an Akt protein or a nucleic acid encoding for an angiogenic growth factor or an Akt protein, are preferably administered locally to a site requiring angiogenesis via direct injection or intraarterially via catheter delivery. By 'direct injection' it is meant that a syringe or needle is used to intramuscularly or subcutaneously inject the pharmaceutical composition to the desired site using standard injection techniques. By 'catheter delivery' it is meant that the pharmaceutical composition is delivered intraarterially using any type of balloon catheter well know in the art, including, for example, double balloon catheters, porous balloon catheters and hydrogel coated balloon catheters (see e.g. Riessen, R. et al., *J. Am. Coll. Cardiol.*, 23(5): 1234–1244, 1994).

These and other aspects of the invention, as well as various advantages and utilities, will be more apparent with reference to the detailed description of the preferred embodiments.

BRIEF DESCRIPTION OF THE BRIEF DRAWINGS

The Examples may include reference to one or more drawings that may or may not be present. It is to be understood that none of the drawings referenced in this application are required for enablement of the invention as disclosed herein.

Example 1—Figure Legends

Figure 5A:
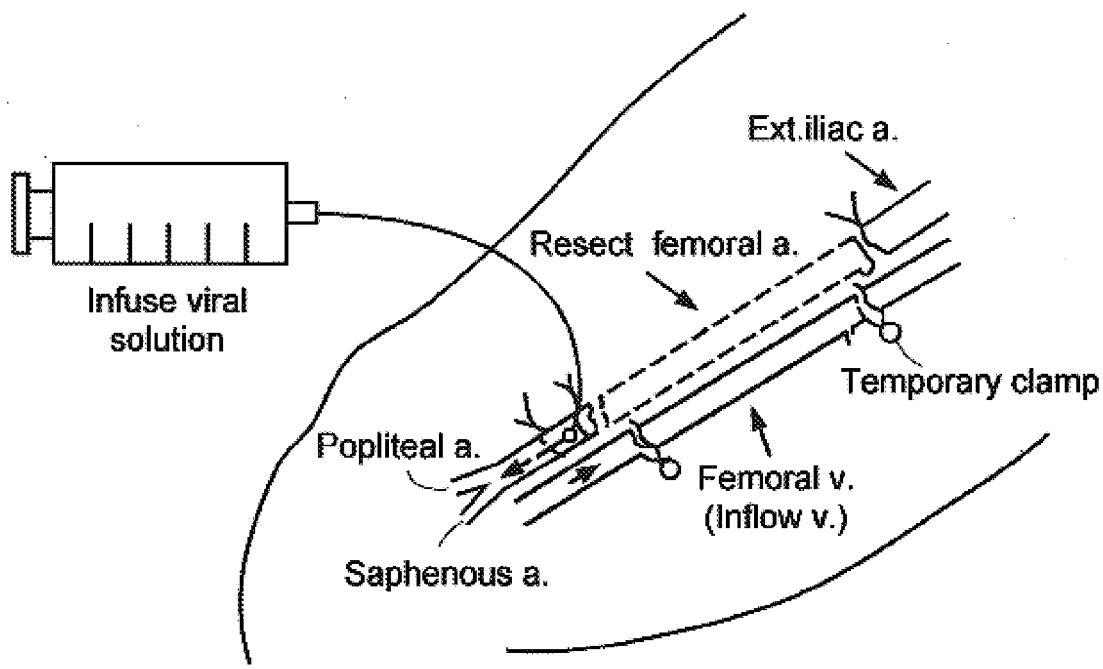
Figure 5B:
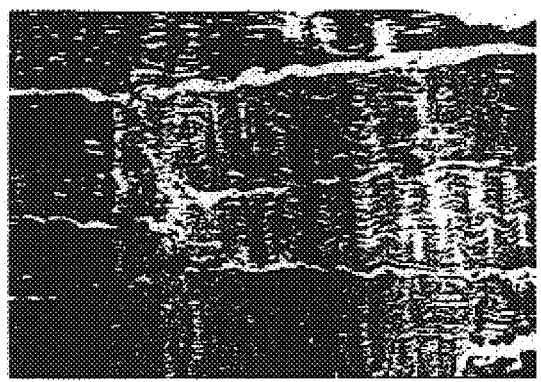
Figure 5C:
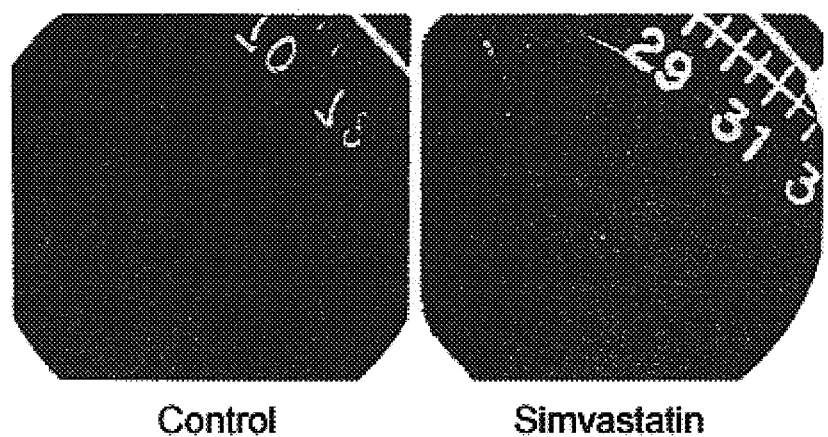
Figure 5D:
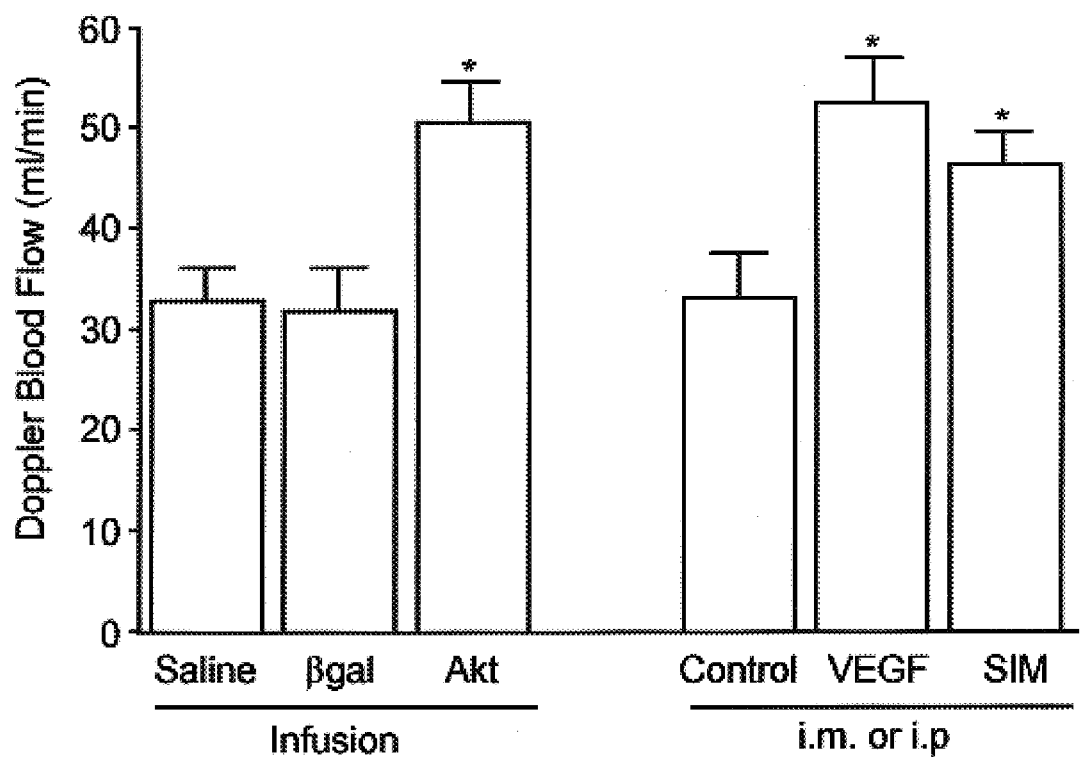
Figures 1, 5E:
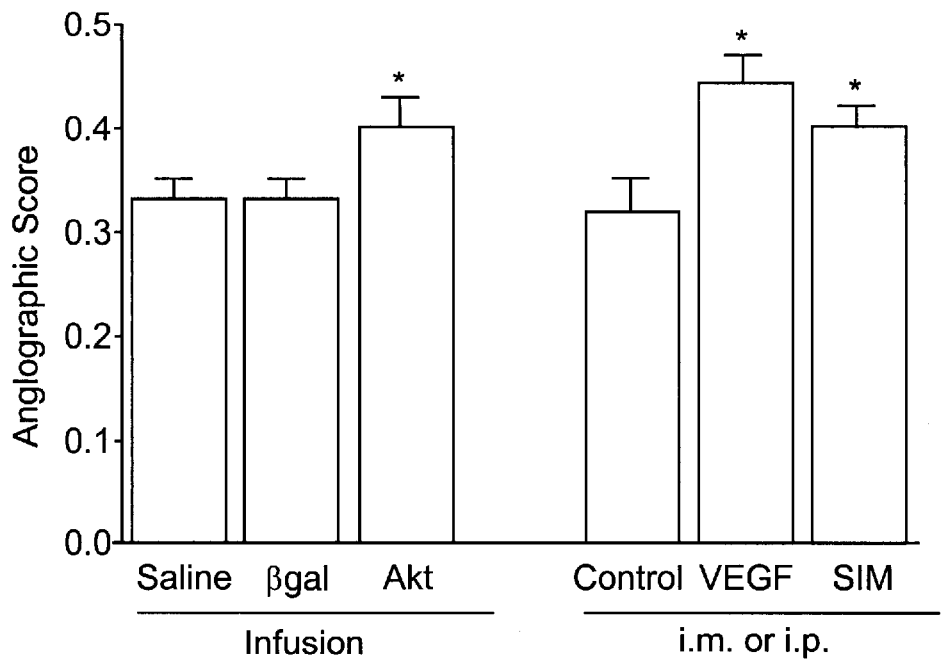

FIG. 1. Simvastatin increases Akt phosphorylation in endothelial cell.

FIGS. 1a–e depict representative Western immunoblots of the effects of simvastatin on Akt phosphorylation level under various conditions. a, Dose-dependent phosphorylation of Akt by simvastatin. b, Time-dependent changes in Akt phosphorylation at serine 473 following stimulation by simvastatin (1 μM). C, Reversal of simvastatin-induced Akt phosphorylation by mevalonate (200 μM). d, Sensitivity of simvastatin-induced Akt phosphorylation to wortmannin. e, Sensitivity of simvastatin- and VEGF-induced Akt phosphorylation to LY294002. The extent of Akt phosphorylation was detected by anti-phosphorylated serine 473 residue of Akt1 specific antibody (PhosphoAkt (Ser 473)). HUVEC were treated with simvastatin for 30 minutes except for time course experiment shown in 1a. In c, d, and e, HUVEC were pretreated with mevalonate (200 μM) wortmannin (500 nM) or LY294002 (10 μM) for 1 hour, prior to 30 minutes stimulation with 1 μM simvastatin or 100 ng/ml VEGF.

Figures 2, 5E:
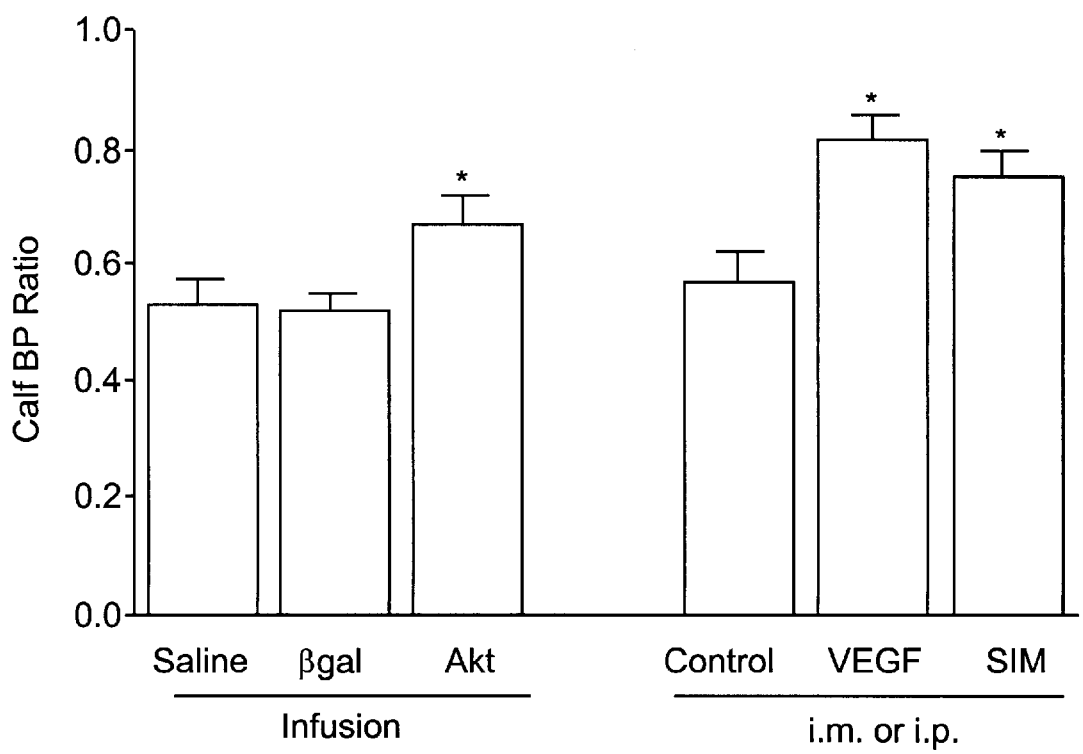

FIG. 2. Simvastatin stimulates Akt polypeptide kinase activity.

Figure 2A:
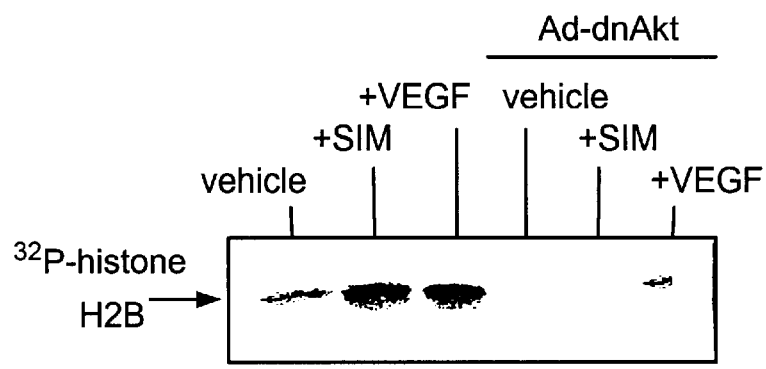

FIG. 2a depicts a representative autoradiogram of phosphorylation histone H2B (2 μg) by immunoprecipitated Akt. Akt was immnunoprecipitated from lysate prepared HUVEC treated with simvastatin (SIM) or 100 ng/ml VEGF for 30) min. Under some conditions, cells were transfected with an adenovirus construct encoding dominant negative form of Akt1 (Ad-dnakt) 24 hours prior to drug treatment. Immunoprecipitated Akt was incubated with histone H2B (2 μg) for 30 minutes at 30° C. and reaction was terminated by adding SDS-sample buffer. Proteins were separated by SDS-PAGE and the extent of histone H2B phosphorylation was visualized by autoradiography.

Figure 2B:
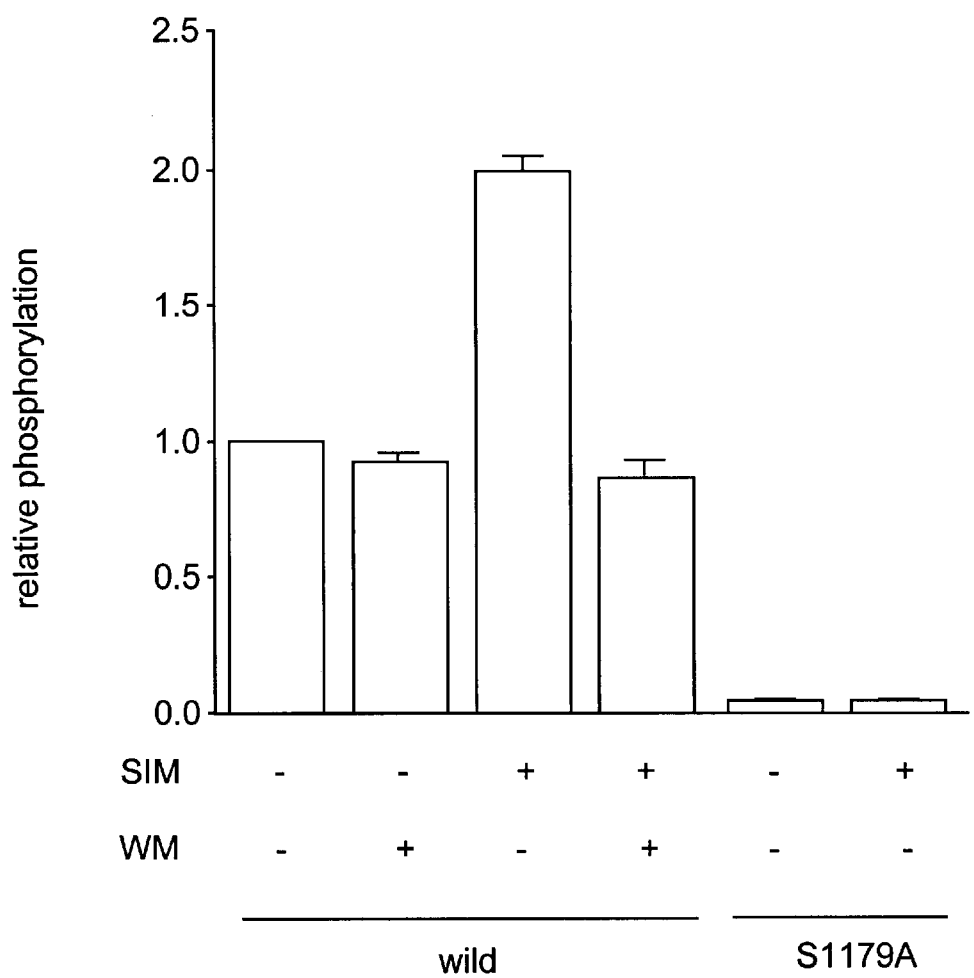

FIG. 2b shows an analysis of Akt polypeptide kinase activity toward eNOS peptides. Akt was immunoprecipitated and incubated with 25 μg eNOS peptide (wild: eNOS peptide corresponding to positions including its functional site serine 1179 residue. S1179A: the mutant peptide where the serine residue phosphorylated by Akt changed to alanine). Treatment with wortmannin (WM, 500 nM) was performed 1 hour prior to addition of simvastatin. Results are presented as mean ±S.E.M. (n=5–7, *p<0.05).

Figures 3, 5E:
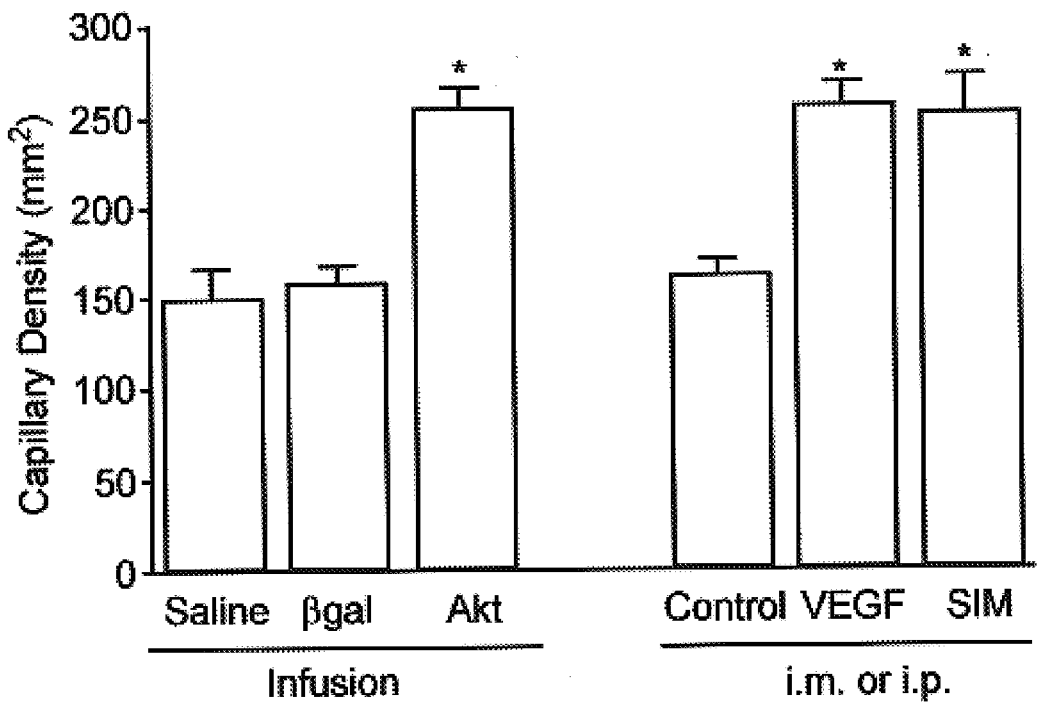

FIG. 3. Simvastatin induces Akt-mediated phosphorylation of eNOS in vivo.

FIG. 3 depicts representative autoradiograms of phosphorylation of eNOS by Akt under various conditions. a, Simvastatin (SIM) increases phosphorylation of endogenous eNOS, which is abrogated by overexpression of dominant negative Akt1. HUVEC were radiolabeled with $^{32}$P-orthophosphate and stimulated with simvastatin (1 μM) or VEGF (100 ng/ml) for 30 min. Alternatively, HUVEC were infected with adenovirus expressing constitutively-active Akt (myrAkt) 24 hours prior to radiolabeling and assayed for endogenous eNOS phosphorylation in the absence of Akt agonist. Parallel cultures were mock-infected or infected with adenovirus encoding dominant-negative Akt (Ad-dnAkt) 24 hours prior to simvastatin or VEGF activation. b, Simvastatin-induced eNOS phosphorylation is sensitive to wortmannin. After 1 hour pretreatment with 500 nM wortmannin, HUVEC were stimulated with simvastatin or VEGF in the presence or absence of 500 mM wortmannin. Wortmannin was added to cultures 1 hour prior to stimulation with simvastatin or VEGF. Endogenous eNOS protein was immunoprecipitated, separated by SDS-PAGE, and its phosphorylation was visualized by autoradiography. c, COS-7 cells co-transfected with eNOS (wt: wildtype eNOS, S1179A: serine 1179 mutant) and Akt (HA-Akt) expression plasmids. Following transfection, cells were incubated in serum-depleted media for 48 hours and then subjected to radiolabeling with $^{32}$P-orthophosphate and treatment with wortmannin and simvastatin. Immunoprecipitates of wildtype or mutant eNOS were examined for $^{32}$P-phosphate incorporation by autoradiography following SDS-PAGE.

FIG. 4. Simvastatin promotes endothelial cell survival through an Akt-dependent pathway.

Figure 4A:
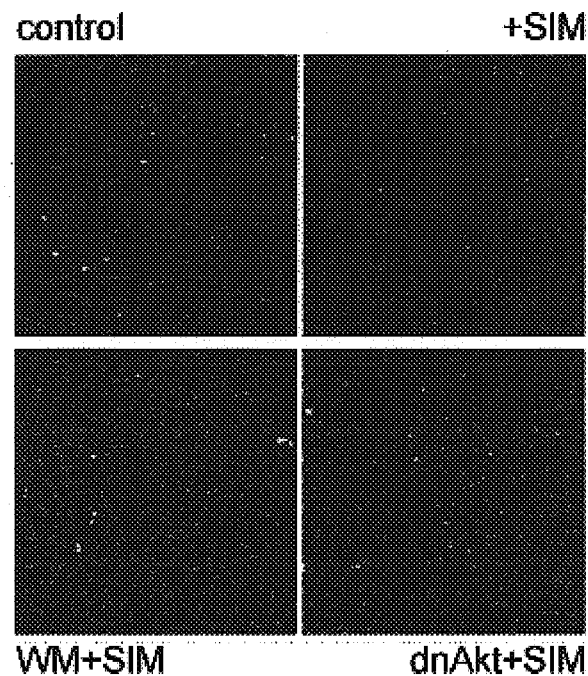

FIG. 4a depicts representative images showing the cell-survival effects by simvastatin as detected by double-staining with Annexin-V (green) and propidium iodide (red). HUVEC cultures were plated on chamber slides at a density of 4×10$^4$ cells/well. HUVEC were incubated in serum-depleted media for 3 hours and subjected to stimulation with simvastatin (1 μM) for an additional 5 hours. Parallel cultures were infected with an adenoviral construct expressing dominant-negative Akt (dnAKT) 24 hours prior to the change to serum-free media. Some cultures were treated with 500 nM wortmannin (WM) for 1 hour prior to each stimulation with simvastatin.

Figure 4B:
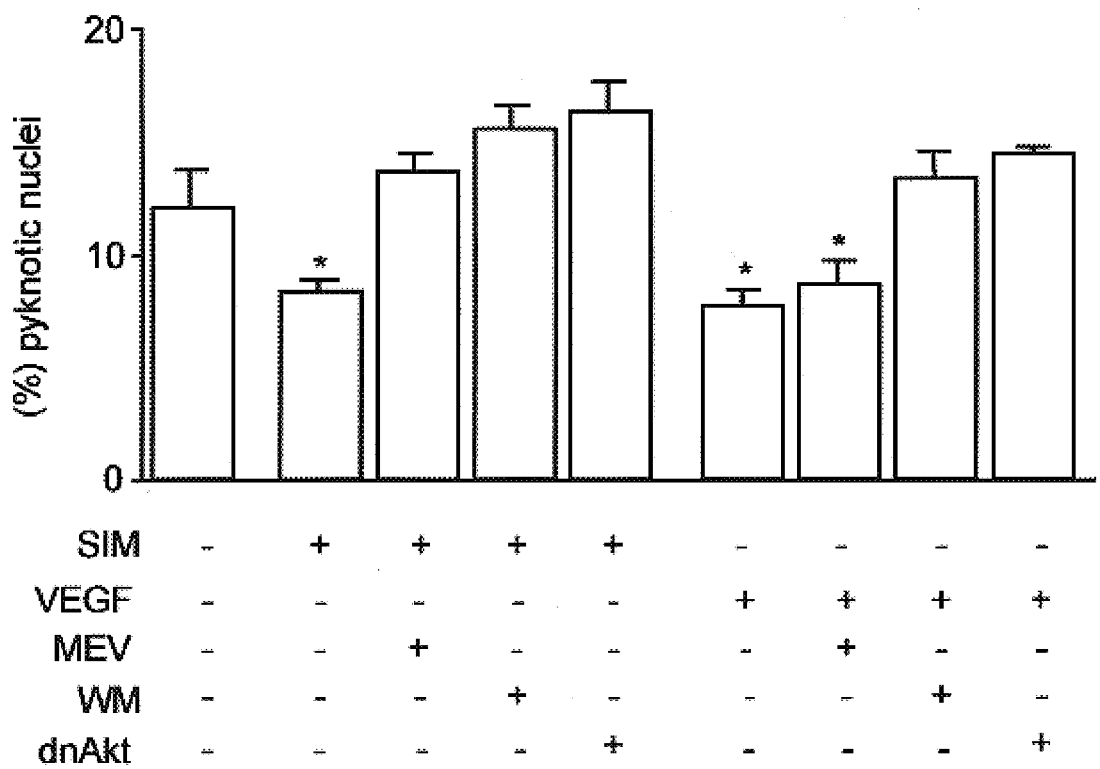

FIG. 4b shows quantitative analysis of simvastatin-promoted endothelial survival by counting pyknotic nuclei stained by Hoechst 33342. HUVEC were examined in serum-free media as described above to assess the effects of 1 μM simvastatin (SIM) or VEGF (100 μg/ml) on survival. Data are shown as the mean ±S.E.M. (n=4–6, *p<0.05).

FIG. 5. Statin administration or enhanced Akt signaling in endothelial cells promotes blood vessel formation and improves hemodynamic deficiency in the rabbit hindlimb in response to unilateral femoral artery resection.

FIG. 5a shows a diagram of the experimental method. The femoral artery and its major branches were dissected. Adenovirus-mediated gene transfer to the endothelium was achieved by infusing saline containing Adeno-βgal or Adeno-myrAkt through the distal end of the femoral artery and incubation for 15 minutes in the limb by temporarily clamping the femoral vein.

FIG. 5b shows a section of gastrocnemius muscle stained with X-gal. Gastrocnemius muscle was excised 3 days after surgery and perfusion with Adeno-βgal, and stained with X-gal to determine transgene distribution in hematoxylin and eosin-stained tissue.

FIG. 5c shows an internal iliac angiography which was performed on the different treatment groups to assess collateral vessel formation. Angiograms at 40 days after femoral artery resection showing enhanced collateral vessel formation in animals that received 0.1 mg/kg/d of simvastatin by intraperitoneal injection (i.p.) relative to control animals that underwent surgery but received no other treatment. Quantitative measurements of collateral vessels were performed on the control group, the simvastatin-treated group and a group that received an intramuscular (i.m.) of Adeno-VEGF. Angiographic score was also assessed in the experimental groups receiving infusions of saline, Adeno-βgal or Adeno-myrAkt at 31 days after surgery.

FIG. 5d shows a graph depicting the blood flow in the treated limbs. Blood flow was quantified in the surgically-treated limbs of the different treatment groups using a Doppler guidewire probe. Doppler measurements were made under conditions of maximal flow achieved by the infusion of 2 mg papaverine.

FIG. 5e shows a graph depicting the calf blood pressure ratio in the treated limbs. The calf blood pressure ratio was calculated as the systolic pressure of the surgically-treated limb divided by that of the normal limb for each animal.

Figure 5F:
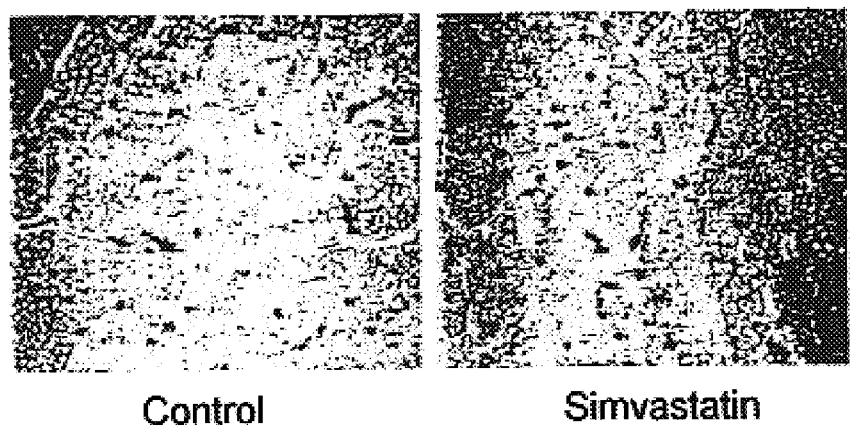

FIG. 5f shows a section of alkaline phosphate stained adductor muscle from treated and control animals and a graph representing the data from the sections. Alkaline phosphatase staining of the adductor muscle from ischemic limbs showing greater capillary density in the simvastatin-treated animals than in control animals at 40 days post-surgery. Average capillary density for all experimental groups is reported. Data in each experiment are presented as mean±S.E.M., (n=6 rabbits for each treatment group, *p<0.05 relative to the saline-infused or control groups compared by one-way analysis of variance).

DETAILED DESCRIPTION OF THE INVENTION

To understand the mechanism by which VEGF promotes new blood vessel formation (angiogenesis), we have analyzed the signaling pathways downstream from this growth factor. In particular, we have analyzed Akt signaling in endothelial cells. Akt (also known as Protein Kinase-B, PKB) inhibits apoptotic cell-death of cells, and in particular, inhibits apoptotic cell-death of cardiomyocytes, skeletal myocytes and/or vascular endothelial cells. (See, e.g., U.S.

Ser. No. 9/922,633, entitled, "Akt Compositions for Enhancing Survival of Cells", PCT Application No. PCT/US99/22633, published as WO 00/20025). In the course of analyzing Akt signaling events in an animal model of ischemia, we have discovered that activation of Akt signaling in endothelial cells is sufficient to promote angiogenesis. We also have discovered that simvastatin (an HMG CoA reductase inhibitor) is a potent activator of Akt. In view of these discoveries, we believe that simvastatin, as well as other HMG CoA reductase inhibitors, can be used to promote angiogenesis in tissues, and that such inhibitors are useful for treating conditions in which new blood vessel growth is desirable to treat the condition.

According to one aspect of the invention, a method for promoting angiogenesis in a tissue of a subject in need of such treatment is provided. The method involves administering to the subject, an HMG CoA reductase inhibitor in an amount effective to promote angiogenesis in the tissue, wherein the subject is not otherwise in need of administration of an HMG CoA reductase inhibitor. According to this aspect, the subject may or may not be hyperlipidemic and/or hypercholesterolemic. In certain embodiments, the method further includes the step of detecting angiogenesis in the tissue.

Conditions that can be treated in accordance with this method of the invention (administration by any route, preferably oral administration) are conditions characterized by insufficient vascularization (or predisposition thereto) of the affected tissue, i.e., conditions in which neovascularization, rather than nitric oxide (NO)-mediated vasodilation, is needed to achieve sufficient vascularization in the affected tissue, and that are selected from the following group of conditions: (1) diabetic ulcers, (2) gangrene, (3) surgical or, other wounds requiring neovascularization to facilitate healing; (4) Buerger's syndrome; (5) hypertension; (6) ischemic diseases including, for example, cerebrovascular ischemia, renal ischemia, pulmonary ischemia, limb ischemia, ischemic cardiomyopathy, myocardial ischemia, ischemia of tissues such as, for example, muscle, brain, kidney and lung; and other conditions characterized by a reduction in microvasculature. The preferred method of treatment further includes the step of detecting angiogenesis in the affected tissue following treatment. Exemplary tissues in which angiogenesis can be promoted and, optionally, detected in accordance with this method of the invention include: ulcers (e.g., diabetic ulcers); surgical wounds; ischemic tissue, i.e., a tissue having a deficiency in blood as the result of an ischemic disease including, for example, muscle, brain, kidney and lung; ischemic diseases including, for example, cerebrovascular ischemia, renal ischemia, pulmonary ischemia, limb ischemia, ischemic cardiomyopathy and myocardial ischemia. In the preferred embodiments, the HMG CoA reductase inhibitor is a statin molecule. More preferably, the statin molecule(s) is orally administered.

According to yet another aspect of the invention, a method for promoting angiogenesis in a tissue of a subject is provided. The method involves locally administering to the tissue, an HMG CoA reductase inhibitor in an amount effective to promote angiogenesis in the tissue. Preferably, the subject is not otherwise in need of administration (particularly, local administration) of an HMG CoA reductase inhibitor. According to certain embodiments, the subject is hyperlipidemic and/or hypercholesterolemic. According to yet other embodiments, the subject is nonhyperlipidemic and/or nonhypercholesterolemic.

Conditions that can be treated in accordance with this method of the invention (locally administered) are conditions characterized by insufficient vascularization of the affected tissue, i.e., conditions in which neovascularization, rather than nitric oxide (NO)-mediated vasodilation, is needed to achieve sufficient vascularization in the affected tissue. The methods and compositions of the invention involve locally administering the compositions of the invention to the tissue. Preferably, the subject is not otherwise in need of administration (particularly, local administration) of an HMG CoA reductase inhibitor.

Exemplary conditions that can be treated in accordance with the methods of the invention include: (1) severe occlusive and/or obstructive vascular disease, such as (a) peripheral vascular disease (particularly, diabetic peripheral vascular disease), (b) myocardial ischemia/myocardial infarction, (c) coronary artery disease, (d) cerebral vascular disease, (e) visceral vascular disease; and (2) surgical or other wounds requiring neovascularization to facilitate healing. Accordingly, the preferred method of treatment further includes the step of detecting angiogenesis in the affected tissue following treatment. Exemplary tissues to which the HMG CoA reductase inhibitor can be administered in accordance with the methods of the invention to promote angiogenesis therein include cardiac tissue, ulcers (e.g., diabetic ulcers), surgical wounds, neuronal tissue (e.g., tissue damaged incident to ischemia of the brain), and other tissue damaged as a result of severe occlusive and/or obstructive vascular disease or injury (would healing).

The HMG CoA reductase inhibitors of the invention are particularly useful for activating Akt polypeptides in vivo to trigger the signaling events which result in angiogenesis. Accordingly, the methods of the invention, in general, involve administering to the subject an isolated HMG CoA reductase inhibitor(s) in an amount and in a manner effective to promote angiogenesis in a tissue of the subject. Preferably, this amount also is sufficient to activate Akt polypeptides to inhibit apoptotic cell-death of vascular endothelial cells.

A "hyperlipidemic" subject is both a hypercholesterolemic and a hypertriglyceridemic subject. The current criteria established for human subjects are well known in the art (See, e.g., Harrison's Principles of Experimental Medicine, 13th Edition, McGraw-Hill, Inc., New York.). Hypercholesterolemic subjects and hypertriglyceridemic subjects are associated with increased incidence of premature coronary heart disease including vascular endothelial cell dysfunction. A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity high lipoprotein (a), and personal history of cerebrovascular disease or occlusive peripheral vascular disease. A hypertriglyceridemic subject has a triglyceride (TG) level of >250 mg/dL. Thus, a hyperlipidemic subject is defined as one whose cholesterol and triglyceride levels equal or exceed the limits set as described above for both the hypercholesterolemic and hypertriglyceridemic subjects. Conversely, a nonhyperlipidemic subject has cholesterol and/or triglyceride levels which fall below the foregoing levels to a statistically significant extent, as defined in the above-cited medical literature.

The HMG CoA reductase inhibitors of the invention are administered in effective amounts. An effective amount is a dosage of the HMG CoA reductase inhibitor(s) sufficient to provide a medically desirable result. In general, a therapeutically effective amount means that amount necessary to delay the onset of, inhibit the progression of, or halt altogether the particular condition being treated. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. More preferably, a therapeutically effective amount varies from about 0.5 mg/kg/day to about 10 mg/kg/day.

The therapeutically effective amount of the isolated HMG CoA reductase inhibitors is that amount effective to promote angiogenesis and, preferably, activate Akit to inhibit apoptotic cell-death of a cardiomyocyte, a skeletal myocyte, or a vascular endothelial cell. Therapeutically effective amounts can be determined using, for example, standard tests known in the art. For example, TUNEL staining, and the appearance of condensed chromatin and other morphological features characteristic of apoptosis in electron micrographs can be used to assess apoptosis in the cells of the invention and other cell types.

A number of laboratory tests to detect angiogenesis, well known in the art, are described, for example, in Harrison's: Principles of Internal Medicine (McGraw Hill, Inc., New York). Generally, the tests may be divided into four main categories: (1) nonspecific indexes of tissue necrosis and inflammation in a biopsy specimen, (2) electrocardiograms, (3) serum enzyme changes (e.g., creatine phosphokinase levels), and (4) blood vessel imaging. Specifically, as described herein, angiogenesis can be determined by limb blood pressure measurement, quantitative angiography, intravascular doppler blood flow measurements and capillary density evaluation in a biopsy specimen. A person of ordinary skill in the art could easily apply any of the foregoing tests to determine when a subject is at risk, is suffering, or has suffered, a severe vascular occlusion or obstruction. A positively identified subject would thus benefit from a method of treatment of the invention.

The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with occlusive or obstructive vascular disorderes, an effective amount is that amount which engenders sufficient neovascularization or angiogenesis so as to provide an increase in blood flow to the ischemic region. Likewise, an effective amount for treating a wound would be an amount sufficient to engender sufficient neovascularization or angiogenesis so as to promote wound healing. Thus, it will be understood that the HMG CoA reductase inhibitors of the invention can be used to treat the above-noted conditions prophylactically in subjects at risk of developing the foregoing conditions. By "acutely" it is meant that the HMG CoA reductase inhibitors of the invention are administered immediately and according to the preferred modes of administration of the particular disorder being treated. For example, in connection with myocardial infarction or myocardial ishcemia, the HMG CoA reductase inhibitors may be administered to a subject in need of such treatment preferably by intra-coronary (and optionally including cross-clamping of the aorta) or preferably intramyocardial injection (see e.g., Hajjar R J, et al., *Proc Natl Acad Sci U S A*, 1998, 95:5251–5256; Vincent, C. K., et al., *Mol. Cell. Biol.*, 1993, 13: 1264–1272). As used in the claims, "inhibit" embraces preventing and/or reducing in all of the foregoing. It is preferred generally that a maximum dose be used, that is, the highest safe dose according to sound medical judgment.

A subject, as used herein, refers to any mammal (preferably a human, and including a non-human primate, cow, horse, pig, sheep, goat, dog, cat or rodent) that may be susceptible to a condition in which angiogenesis is the only adequate remedy to treat the condition. Preferably the mammal is otherwise free of symptoms calling for treatment with an HMG CoA reductase inhibitor. Reported conditions that have symptoms calling for treatment with activated Akt molecules are also included within the scope of the invention.

The preferred subjects to whom the HMG CoA reductase inhibitors can be administered orally or locally are subjects having (or a predisposition to) hypertension, diabetic ulcers, gangrene, surgical or other wounds requiring neovascularization to facilitate healing, Buerger's syndrome; ischemia of the muscle, brain, kidney, lung, heart or limb and other conditions characterized by a reduction in microvasculature.

The methods of the invention involve contacting a cell type of choice with an HMG CoA reductase inhibitor under conditions to permit activation of the Akt molecule in the cell type of choice. In certain embodiments, the contacting of a cell type of choice with an HMG CoA reductase inhibitor according to the invention can comprise either acute or prophylactic administration of the HMG CoA reductase inhibitor. Such acute and/or prophylactic administration of the HMG CoA reductase inhibitor is particularly contemplated when the cell type of choice according to the invention contacted with the HMG CoA reductase inhibitor, is part of a tissue or an organ scheduled to be transplanted or implanted. Administration of the HMG CoA reductase inhibitors allows for longer term survival of the cells of the transplanted (implanted) tissue and/or organ and/or angiogenesis in the tissue under the adverse conditions the tissue and/or organ is subjected to during such procedure, i.e., ischemia, lower temperature, reperfusion, etc, therefore improving the tissue/organ's viability and/or acceptance by the recipient organism.

According to the invention, the method involves locally administering to a subject an HMG CoA reductase inhibitor in an amount effective to promote angiogenesis in the undervascularized tissue of the subject. The treatment can be partiuclarly useful in cases where blood supply to the undervascularized tissue is caused by a severe occulsion or obstruction. By "a severe occlusion or obstruction" it is meant that the subject is at risk of developing, is currently having, or has suffered a severe occlusion or obstruction resulting in a significant reduction in blood supply. Immediate administration of an HMG CoA reductase inhibitor would greatly benefit the subject by promoting angiogenesis in the tissue prior to, or following the infarct. By "immediate" it is meant that administration occurs before (if it is diagnosed in time), or within 48 hours from detection of the severe obstruction or occlusion, although administration up to 14 days after the episode may also be beneficial to the subject.

Prolonged or chronic administration of an HMG CoA reductase inhibitor may also be used to treat a patient in need of increased angiogenesis. Prolonged administration would involve treatment of the patient for several months to several years. Chronic treatment would involve life-long treatment of the patient. The necessity for an immediate, prolonged or chronic administration of an HMG CoA reductase inhibitor would be determined on an individual basis depending on the particular condition of the patient. One skilled in the art would readily be able to determine whether immediate, prolonged or chronic administration was necessary.

Exemplary severe occlusive and/or obstructive vascular conditions that can be treated in accordance with the methods of the invention include peripheral vascular diseases (e.g., diabetic peripheral vascular disease), myocardial ischemia/myocardial infarction, coronary artery disease, cerebral vascular disease, visceral vascular disease, etc. Methods for detecting such conditions and assessing the efficacy of the treatment method are described in, e.g., Harrison's Principles of Experimental Medicine, 13th Edition, McGraw-Hill, Inc., New York.

An HMG CoA reductase inhibitor is a term of art which refers to a molecule which inhibits the enzyme HMG-CoA reductase and, therefore, inhibits the synthesis of cholesterol. As used herein, the HMG CoA reductase inhibitors that are useful in accordance with the methods of the invention satisfy the conventional meaning of this phrase and, further, are capable of activating Akt signaling in vascular endothelial cells. As used herein, "activating Akt signaling" refers to inducing a change in the Akt polypeptide that is sufficient to promote angiogenesis when the activation occurs in vivo. In general, the change that is induced is phosphorylation of the Akt polypeptide, typically at Ser 473 and/or Thr 308.

Exemplary HMG CoA reductase inhibitors are provided below. The detailed description also provides screening assays for selecting putative inhibitors which also are capable of activating Akt signaling in vascular endothelial cells. The preferred HMG CoA reductase inhibitors that are useful in accordance with the methods and compositions of the invention are statin molecules. These include: Lovastatin (Mevacor), Pravastatin (Pravachol), Simvastatin (Zocor), Fluvastatin (Lescol), Atorvastatin (Lipitor), or Cerivastatin (Baycol), provided that when the statin molecule is an inhibitor of HMG CoA, it is processed into the corresponding lactone form prior to local administration.

There are a large number of compounds described in the art that have been obtained naturally or synthetically, which have been seen to inhibit HMG-CoA reductase, and which form the category of agents useful for practicing the present invention. Traditionally these agents have been used to treat individuals with hypercholesterolemia. Examples include some which are commercially available, such as simvastatin (U.S. Pat. No. 4, 444,784), lovastatin (U.S. Pat. No. 4,231, 938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. No. 5,622,985; U.S. Pat. No. 5,135,935; U.S. Pat. No. 5,356,896; U.S. Pat. No. 4,920,109; U.S. Pat. No. 5,286,895; U.S. Pat. No. 5,262,435; U.S. Pat. No. 5,260,332; U.S. Pat. No. 5,317,031; U.S. Pat. No. 5,283,256; U.S. Pat. No. 5,256,689; U.S. Pat. No. 5,182,298; U.S. Pat. No. 5,369,125; U.S. Pat. No. 5,302,604; U.S. Pat. No. 5,166,171; U.S. Pat. No. 5,202,327; U.S. Pat. No. 5,276,021; U.S. Pat. No. 5,196,440; U.S. Pat. No. 5,091,386; U.S. Pat. No. 5,091,378; U.S. Pat. No. 4,904,646; U.S. Pat. No. 5,385,932; U.S. Pat. No. 5,250,435; U.S. Pat. No. 5,132,312; U.S. Pat. No. 5,130,306; U.S. Pat. No. 5,116,870; U.S. Pat. No. 5,112,857; U.S. Pat. No. 5,102,911; U.S. Pat. No. 5,098,931; U.S. Pat. No. 5,081,136; U.S. Pat. No. 5,025,000; U.S. Pat. No. 5,021,453; U.S. Pat. No. 5,017,716; U.S. Pat. No. 5,001,144; U.S. Pat. No. 5,001,128; U.S. Pat. No. 4,997,837; U.S. Pat. No. 4,996,234; U.S. Pat. No. 4,994,494; U.S. Pat. No. 4,992,429; U.S. Pat. No. 4,970,231; U.S. Pat. No. 4,968,693; U.S. Pat. No. 4,963,538; U.S. Pat. No. 4,957,940; U.S. Pat. No. 4,950,675; U.S. Pat. No. 4,946,864; U.S. Pat. No. 4,946,860; U.S. Pat. No. 4,940,800; U.S. Pat. No. 4,940,727; U.S. Pat. No. 4,939,143; U.S. Pat. No. 4,929,620; U.S. Pat. No. 4,923,861; U.S. Pat. No. 4,906,657; U.S. Pat. No. 4,906,624; and U.S. Pat. No. 4,897,402, the disclosures of which patents are incorporated herein by reference.

Additional patents which disclose HMG CoA reductase inhibitors and which are incorporated by reference include: U.S. Pat. No. 6,043,064; Re 36,520; Re 36,481; U.S. Pat. No. 6,001,618; U.S. Pat. No. 5,948,435; U.S. Pat. No. 5,877,208; U.S. Pat. No. 5,792,461; U.S. Pat. No. 5,620,876; U.S. Pat. No. 5,523,460; U.S. Pat. No. 5,475,029; U.S. Pat. No. 5,173,487; U.S. Pat. No. 5,177,080; U.S. Pat. No. 5,189,180; U.S. Pat. No. 5,177,104; U.S. Pat. No. 5,202,327; U.S. Pat. No. 5,250,435; U.S. Pat. No. 5,260,440; U.S. Pat. No. 5,256,692; U.S. Pat. No. 5,266,707; U.S. Pat. No. 5,264,455; U.S. Pat. No. 5,369,123; U.S. Pat. No. 5,371,077; U.S. Pat. No. H1,286; U.S. Pat. No. 5,308,864; U.S. Pat. No. 5,110,825; U.S. Pat. No. 5,106,992; U.S. Pat. No. 5,102,893; U.S. Pat. No. 5,099,035; U.S. Pat. No. 5,098,931; U.S. Pat. No. 5,089,523; U.S. Pat. No. 5,081,136; U.S. Pat. No. 5,075,311; U.S. Pat. No. 5,053,525; U.S. Pat. No. 5,049,696; U.S. Pat. No. 5,032,602; U.S. Pat. No. 5,025,017; U.S. Pat. No. 5,021,453; U.S. Pat. No. 5,010,105; U.S. Pat. No. 5,001,148; U.S. Pat. No. 4,997,837; U.S. Pat. No. 4,997,658; U.S. Pat. No. 4,992,462; U.S. Pat. No. 4,970,231.; U.S. Pat. No. 4,970,221; U.S. Pat. No. 4,968,693; U.S. Pat. No. 4,957,971; U.S. Pat. No. 4,957,940; U.S. Pat. No. 4,950,675; U.S. Pat. No. 4,940,800; U.S. Pat. No. 4,937,263; U.S. Pat. No. 4,937,259; U.S. Pat. No. 4,929,620; U.S. Pat. No. 4,923,861; U.S. Pat. No. 4,920,111; U.S. Pat. No. 4,916,162; U.S. Pat. No. 4,906,657; U.S. Pat. No. 4,906,624; U.S. Pat. No. 4,897,402; U.S. Pat. No. 4,885,314; U.S. Pat. No. 4,876,366; U.S. Pat. No. 4,876,279; U.S. Pat. No. 4,868,185; U.S. Pat. No. 4,866,090; U.S. Pat. No. 4,866,068; U.S. Pat. No. 4,864,038; U.S. Pat. No. 4,857,547; U.S. Pat. No. 4,857,546; U.S. Pat. No. 4,855,321; U.S. Pat. No. 4,851,436; U.S. Pat. No. 4,847,306; U.S. Pat. No. 4,808,621; U.S. Pat. No. 4,792,614; U.S. Pat. No. 4,782,084; U.S. Pat. No. 4,772,626; U.S. Pat. No. 4,771,071; U.S. Pat. No. 4,766,145; U.S. Pat. No. 4,761,419; U.S. Pat. No. 4,738,982; U.S. Pat. No. 4,735,958; U.S. Pat. No. 4,719,229; U.S. Pat. No. 4,681,893; U.S. Pat. No. 4,668,699; U.S. Pat. No. 4,665,091; U.S. Pat. No. 4,661,483; U.S. Pat. No. 4,654,363; U.S. Pat. No. 4,647,576; and U.S. Pat. No. 4,567,289.

The preferred methods of treatment depend upon the particular aspect of the invention, i.e., the type of subject being treated. For a subject having a condition selected from the group consisting of hypertension, diabetes, gangrene, wounds, Buerger's syndrome, and other conditions characterized by a reduction or obstruction in microvasculature, administration of the HMG CoA reductase inhibitor can be by any route, with oral administration particularly preferred. For a subject having a condition that results from a severe occlusive and/or obstructive vascular tissue, administration involves locally administering the HMG CoA reductase to the tissue of a subject. In either instance, the HMG CoA reductase inhibitor is administered in an amount effective to promote angiogenesis in the affected tissue of the subject. In certain embodiments, locally administering involves inserting a stent containing the HMG CoA reductase inhibitor into the tissue. Alternatively, locally administering involves administering to the subject a pharmaceutical composition containing an HMG CoA reductase inhibitor and a pharmaceutically acceptable carrier. In certain preferred embodiments, the pharmaceutical composition is suitable for topical application or internal applications and can be formulated as a salve, a gel or a patch. Preferably, the pharmaceutical composition is a controlled release matrix and, more preferably, the composition is formulated to release the HMG CoA reductase inhibitor substantially continuously for a period of at least one day. Exemplary controlled release formulations for delivering an HMG CoA reductase inhibitor are reported in U.S. Pat. Nos. 5,376,383 and 4,976,967.

Preferred methods of administration for the HMG CoA reductase inhibitors of the invention into subjects requiring neovascularization (and preferably, subjects also having abnormally elevated apoptotic cell-death of vascular endothelial cells) include intraarterial administration preferably with clamping or locally via a balloon catheter or intraperitoneal injection directly into the affected tissue or wound requiring neovascularization. For example, in the case of intraarterial administration with clamping, the vessel wall in need of such treatment is "isolated" by clamping of the vessel on either side of the "injury" site, resulting in the temporary occlusion of the region to be treated, and allowing local delivery of the HMG CoA reductase inhibitors (e.g., by injection). In the case of intraarterial administration via a balloon catheter, the catheter is preferably of the "soft-hydrogel surface" type.

Preferred methods of administration for the HMG CoA reductase inhibitors of the invention in the treatment of the foregoing diseases include direct intramuscular injection into the myocardium, catheterization of the heart, and intraarterial administration. Intraarterial administration may be accompanied with a permeabilizing agent (e.g., nitric oxide), allowing easier access of the HMG CoA reductase inhibitors of the invention into the myocardium via the circulation.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Intramyocardial administration is preferred in patients suffering form myocardial infarction. Direct application of the compositions of the invention to a wound or to the tissue in the vicinity of the wound is preferred to promote wound healing. Oral administration will be preferred for prophylactic treatment because of the convenience to the patient as well as the dosing schedule. Compositions suitable for oral administration may be presented as discrete units, such as capsules, tablets, lozenges, each containing a predetermined amount of the HMG CoA reductase inhibitors. Other compositions include suspensions in aqueous liquids or non-aqueous liquids such as a syrup, elixir or an emulsion.

The pharnmaceutical compositions may conveniently be presented in unit dosage form and may be prepared by any of the methods well-known in the art of pharmacy. All methods include the step of bringing the HMG CoA reductase inhibitors into association with a carrier which constitutes one or more accessory ingredients. In general, the compositions are prepared by uniformly and intimately bringing the HMG CoA reductase inhibitors into association with a liquid carrier, a finely divided solid carrier, or both, and then, if necessary, shaping the product.

In general, the HMG CoA reductase inhibitors can be administered to the subject (any mammalian recipient) using the same modes of administration that currently are used for administration of other angiogenesis inducers (e.g., VEGF) in humans.

Other delivery systems can include time-release, delayed release or sustained release delivery systems. Such systems can avoid repeated administrations of the HMG CoA reductase inhibitors described above, increasing convenience to the subject and the physician. Many types of release delivery systems are available and known to those of ordinary skill in the art. They include the above-described polymeric systems, as well as polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the HMG CoA reductase inhibitor is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Preparations for parenteral administration include sterile aqueous or non-aqueous solutions suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

According to yet another aspect of the invention, a method for activating an Akt polypeptide is provided. The method involves contacting the Akt polypeptide with an HMG CoA reductase inhibitor in vitro under conditions wherein the HMG CoA reductase inhibitor (preferably a statin molecule as described herein) activates the Akt polypeptide. By "activate" it is meant that the HMG CoA reductase inhibitor facilitates the transformation of the Akt polypeptide from an inactive to an active form. This transition can be determined by detecting various parameters, e.g., degree of Akt polypeptide phosphorylation, degree of phosphorylation of an Akt substrate molecule (e.g. Bad, histone H2B, eNOS etc., or fragments thereof), or other downstream signaling events, including for example a change in the rate of protein degradation, a change in the level of mRNA transcription, a change in the level of protein translation, reduction of apoptosis, induction of angiogenesis, etc. Although not wishing to be bound to any particular theory or mechanism, it is believed that HMG CoA reductase inhibitors facilitate the phosphorylation of the Akt polypeptide (e.g., at Ser 473 and/or Thr 308) which mediates further signaling events that result in angiogenesis in vivo. Thus, in particularly preferred embodiments such as those methods useful as screening assays, the Akt polypeptide that is useful in this aspect of the invention is an Akt polypeptide that is expressed by an endothelial cell. Exemplary Akt polypeptides are described in U.S. Ser. No. 9/922,633, entitled, "Akt Compositions for Enhancing Survival of Cells", PCT Application No. PCT/US99/22633, published as WO 00/20025. Exemplary conditions for performing this aspect of the invention are provided in the Examples.

The human and mouse Akt genes have been isolated and sequenced (Jones P F, et al., *Proc Natl Acad Sci USA*, 1991, 88(10):4171–5; Coffer, P. J. and Woodgett, J. R., *Eur. J. Biochem.*, 1991, 201:475–481; Bellacosa, A., et al., Oncogene, 1993, 8:745–754). See also, Genbank Accession No. M63167 (SEQ. ID NOS. 1 and 2), Genbank Accession No. X61037 (SEQ ID NOS. 3 and 4) for the human Akt cDNA and predicted amino acid sequences, respectively, and Genbank Accession No. X65687 (SEQ ID NOS. 5 and 6) for the mouse Akt cDNA and predicted amino acid sequences, respectively. The skilled in the art will recognize that the results obtained using mouse Akt compositions are predictive of the results that may be obtained using the human sequences, since the mouse c-Akt is 90% homologous to human Akt at the nucleic acid level and 98% homologous at the amino acid level. The c-Akt polypeptide contains, starting from its amino terminus, a src homology 2-like (SH2-like) domain (pleckstrin homology domain), and a kinase domain encoding a serine-threonine kinase with high degree of homology to members of the protein kinase C (PKC) family.

An "Akt molecule", as used herein, embraces both "Akt nucleic acids" and "Akt polypeptides" (discussed below). Akt molecules are capable of promoting angiogenesis in a tissue and inhibiting apoptotic cell-death of cardiomyocytes, skeletal myocytes and vascular endothelial cells both in vivo and in vitro (U.S. Ser. No. 9/922,633, entitled, "Akt Compositions for Enhancing Survival of Cells" and related PCT application as identified above). Preferred examples of Akt molecules are the nucleic acids and polypeptides of, for example, Akt-1, Akt-2, Akt-3, etc.

An "Akt nucleic acid", as used herein, refers to a nucleic acid molecule which: (1) hybridizes under stringent conditions to a nucleic acid having the sequence of SEQ ID NO. 1 and (2) codes for an AKT (i.e., a polypeptide that promotes angiogenesis in vivo and, optionally inhibits apoptotic cell-death of cells, and in particular, inhibits apoptotic cell-death of cardiomyocytes, skeletal myocytes and vascular endothelial cells in vitro or in vivo. Preferably the AKT maintains a serine-threonine kinase activity. The preferred Akt nucleic acid has the nucleic acid sequence of SEQ ID NO. 1. The Akt nucleic acids of the invention also include homologs and alleles of a nucleic acid having the sequence of SEQ ID NO. 1, as well as functionally equivalent fragments, variants, and analogs of the foregoing nucleic acids. "Functionally equivalent", in reference to an Akt nucleic acid fragment, variant, or analog, refers to a nucleic acid that codes for an AKT that promotes angiogenesis in vivo and, optionally, inhibits apoptotic cell-death of cells, particularly apoptotic cell-death of cardiomyocytes, skeletal myocytes and vascular endothelial cells. Preferably the AKT maintains a serine-threonine kinase activity. More specifically, "functionally equivalent" refers to an AKT that has a serine-threonine kinase activity and is capable of promoting angiogenesis in vivo following activation by an HMG CoA reductase inhibitor. Preferably, the activated AKT also is capable of enhancing survival of a cell that may undergo apoptotic cell-death (e.g., a vascular endothelial cell, a cardiomyocyte, a skeletal myocyte).

In one embodiment, the Akt nucleic acid has the nucleotide sequence of SEQ. ID NO 1 ("Akt wild-type nucleic acid"), the nucleotide sequence encoding a "wild-type AKT", i.e., the complete coding sequence of the gene encoding the human Akt.

In the preferred embodiments of the methods, the Akt nucleic acid is selected from the group consisting of a wild-type Akt nucleic acid (e.g., SEQ ID NO. 1, the coding region of SEQ ID NO. 1, SEQ ID NO. 3, and the coding region of SEQ ID NO. 3), and an Akt nucleic acid coupled with a myristoylation/palmitylation sequence, preferably the src myristoylation sequence (Franke, T. F., et al., *Cell*, 1995, 81:727–736). The myristoylation sequence serves as to help target and anchor the AKT onto the cell membrane, thus rendering it constitutively active. The myristoylation sequence may also be placed in a number of different locations within SEQ ID NO. 1, as long as the serine threonine kinase activity of the encoded polypeptide remains intact (see later description of domains).

The Akt nucleic acid is operatively coupled to a promoter that can express Akt in a targeted cell (e.g., a cell selected from the group consisting of a cardiomyocyte, a skeletal myocyte and a vascular endothelial cell). Preferably, the nucleic acid is contained in an appropriate expression vector (e.g., adenoviral vector, modified adenoviral vector, retroviral vector, plasmid, liposome) to more efficiently genetically modify the targeted cell and achieve expression of multiple copies of the AKT. Further details relating to the expression of an Akt nucleic acid are provided in U.S. Ser. No. 9/922,633 and the above-identified related PCT application.

The Akt nucleic acids code for an AKT polypeptide. As used herein, an "AKT" refers to a polypeptide that is coded for by an Akt nucleic acid and/or a structurally related molecule, and preferably has serine-threonine kinase activity. AKTs are useful for inducing angiogenesis in vivo. Preferably, the AKTs also are useful for inhibiting apoptotic cell-death of a cell. The preferred AKT of the invention has the amino acid sequence of SEQ ID NO. 2 (Akt "wild-type" polypeptide) or is a functionally equivalent fragment of SEQ ID NO. 2 (e.g., the partial polypeptide of SEQ ID NO. 4, the polypeptide of SEQ ID NO. 6, etc.). AKTs further include functionally equivalent variants, and analogs of SEQ ID NO. 2, provided that the fragments, variants, and analogs preferably maintain serine-threonine kinase activity, and are capable of inducing angiogenesis. The invention also embraces proteins and peptides coded for by any of the foregoing Akt nucleic acids.

"Structurally related," as used herein, refers to nucleic acids and polypeptides that are homologous and/or allelic to an Akt molecule. In general homologs and alleles typically will share at least 40% nucleotide identity and/or at least 50% amino acid identity to SEQ ID NO: 1 and SEQ ID NO:2, respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://wwww.ncbi.nlm.nih.gov. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The preferred Akt nucleic acids of the invention encode the Akt having the amino acid sequence of SEQ ID NO. 2, the complete polypeptide sequence of the gene encoding the human Akt. This "wild type" human AKT contains starting from its amino terminus, a pleckstrin homology (PH) domain (amino acids 5–108 of SEQ ID NO. 2), and a kinase domain encoding a serine-threonine kinase with high degree of homology to members of the protein kinase C (PKC) family (amino acids 150–408 of SEQ ID NO. 2). It is believed that results obtained using mouse compositions are predictive of the results that may be obtained using the human sequences, since the mouse c-Akt is 98% homologous to human Akt at the amino acid level.

It will be appreciated by those skilled in the art that various modifications of the AKT having the sequence of SEQ ID NO. 2 or functionally equivalent fragments of SEQ ID NO. 2 can be made without departing from the essential nature of the invention. Accordingly, it is intended that polypeptides which have the amino acid sequence of SEQ ID NO. 2 but which include conservative substitutions are embraced within the instant invention. As used herein, "conservative amino acid substitution" refers to an amino acid substitution which does not alter the relative charge or size characteristics of the polypeptide in which the amino acid substitution is made. Conservative substitutions of amino acids include substitutions made amongst amino acids within the following groups: (1) M,I,L,V; (2) F,Y,W; (3) K,R,H; (4) A,G; (5) S,T; (6) Q,N; and, (7) E,D. Fusion proteins, in which a peptide of the invention is coupled to a solid support (such as a polymeric bead), a carrier molecule (such as keyhole limpet hemocyanin), or a reporter group (such as radiolabel or other tag), or a membrane anchoring group (such a myristoylation peptide) also are embraced within the invention.

Preferred AKTs further include myristoylated AKTs. A myristoylation/palmitylation peptide sequence, preferably the src myristoylation peptide sequence, is coupled with the wild type AKT (Franke, T. F., et al., *Cell*, 1995, 81:727–736). The myristoylation sequence helps to target and anchor the AKT onto the cell membrane, thus rendering it constitutively active. Additionally, the myristoylation sequence may be coupled to an AKT, with or without a linker, at any location within the polypeptide as long as the AKT maintains its serine/threonine kinase activity. Moreover, the presence of a PH domain is not necessary for activity. For example, a fusion polypeptide containing the myristoylation sequence and the Akt serine/threonine kinase domain only and in the absence of all, or a part of, a PH domain, can still function to promote angiogenesis and inhibit apoptotic cell-death of the preferred cells of the invention.

Activation of an Akt molecule may be determined by a variety of methods including direct, indirect, in vivo and in vitro assays. For example, a direct method for measuring Akt activity would be phosphorylation of a peptide, polypeptide or protein which is a substrate of an Akt protein kinase. Methods for carrying out and evaluating phosphorylation assays are well known in the art. An indirect method for measuring Akt activity would be by observing a change in the activity of a molcule downstream in the signaling pathway from Akt. For example, Akt phosphorylates and inactivates the forkhead transcription factor. Thus, a construct containing a reporter gene, for example, green florescent protein (GFP), under the control of a forkhead responsive element could be transfected into a cell line of interest. A decrease in the level of GFP expression would indicate an activation of Akt in the cells. In vitro assays would be carried out using purified components outside of a cellular environment while in vivo assay would be carried out using intact cells. Particularly prefered assays for measuring Akt activity would be those assays which are adaptable to a high-throughput format.

According to still another aspect of the invention, a screening method to identify putative HMG CoA reductase inhibitors that activate an Akt polypeptide is provided. The method involves performing an Akt polypeptide activation assay in the presence and absence of a putative HMG CoA reductase inhibitor; and determining the level of Akt polypeptide activation in the presence and absence of the putative inhibitor, wherein an increase in the level of Akt polypeptide activation in the presence of the putative inhibitor relative to the level of Akt polypeptide activation in the absence of the putative inhibitor indicates that the putative inhibitor is an HMG CoA reductase inhibitor as used herein. In preferred embodiments, the cells expressing the Akt polypeptide are selected from the group consisting of cardiac muscle cells (cardiomyocytes), skeletal muscle cells (skeletal myocytes) and vascular endothelial cells.

Putative HMG CoA reductase inhibitors may be isolated from a compound library. Libraries are commercially available or may be constructed by techniques well known in the art. Libraries typically contain at least 100, preferably at least 1,000 and more preferably greater than 100,000 or 1,000,000 different compounds and may be composed of small molecules. peptides, etc. Methods for high throughput screening of libraries to isolate compounds of interest are well know in the art.

According to yet another aspect of the invention, a method for treating a wound (e.g., a surgical wound) is provided. The method involves contacting the wound with a sufficient amount of an HMG CoA reductase inhibitor under conditions wherein the HMG CoA reductase inhibitor enhances healing of the wound. In certain embodiments, contacting the wound involves locally administering the HMG CoA reductase inhibitor to the wound. For example, the HMG CoA reductase inhibitor can be contained in a pharmaceutical composition that is formulated for local administration to a wound or to a tissue in need of neovascularization in a subject.

The HMG CoA reductase inhibitors of the invention may be administered alone or in combination with an additional therapeutic agent, preferably a cytokine or an angiogenic growth factor. Preferred angiogenic growth factors include, for example, acidic and basic fibroblast growth factors, vascular endothelial growth factor, epidermal growth factor, transforming growth factor α and β, platelet-derived endothelial cell growth factor, platelet-derived growth factor, tumor necrosis factor α, hepatocyte growth factor, insulin like growth factor, etc.

The above-described drug therapies are well known to those of ordinary skill in the art and are administered by modes known to those of skill in the art. The drug therapies are administered in amounts which are effective to achieve the physiological goals in combination with the isolated HMG CoA reductase inhibitors of the invention. For example, angiogenic growth factors may be administered as a protein or as a nucleic acid encoding for an angiogenic protein. Preferred angiogenic proteins are those angiogenic proteins which are secreted. Non-secreted angiogenic factor molecules may be engineered so as to contain a secretory signal sequence leading to export of the protein from the cell after production within the cell. Methods for production of a nucleic acid construct containing a gene for an angiogenic growth factor linked to a secretory sequence are well known to those skilled in the art.

An isolated HMG CoA reductase inhibitor may be administered alone or in combination with the above-described drug therapies as part of a pharmaceutical composition. Such a pharmaceutical composition may include the isolated HMG CoA reductase inhibitors in combination with any standard physiologically and/or pharmaceutically acceptable carriers which are known in the art. The compositions should be sterile and contain a therapeutically effective amount of the isolated HMG CoA reductase inhibitors in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the FIMG CoA reductase inhibitors, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

Each of the documents identified herein is incorporated in its entirety herein by reference.

The invention will be more fully understood by reference to the following examples. These examples, however, are merely intended to illustrate the embodiments of the invention and are not to be construed to limit the scope of the invention.

EXAMPLES

Example 1

Introduction

The HMG-CoA reductase inhibitors referred to as statins are widely used cholesterol lowering agents for the treatment of hyperlipidemia. However, recent data suggest additional regulatory pathways within the vasculature may be targeted by these drugs where they function in a protective manner that is independent of their lipid-lowering activity. Here, it is shown that treatment of endothelial cells with simvastatin rapidly activates the serine-threonine protein kinase Akt/PKB, which controls angiogenic responses at the cellular level including endothelial NO production and cell survival. The phosphorylation of the Akt substrate endothelial cell nitric oxide synthase (eNOS) was enhanced by simvastatin in a manner that was inhibited by treatment with PI 3-kinase inhibitors or dominant-negative Akt. Simvastatin treatment stimulated endothelial NO production and inhibited apoptosis. Administration of simvastatin to normocholesterolemic rabbits following femoral artery resection induced angiogenesis and improved perfusion in the ischemic limb. Therefore, activation of the Akt pathway represents a mechanism that can account for some of the beneficial side effects of statins in the cardiovascular system, including the promotion of new blood vessel growth.

Statins inhibit the activity of 3-hydroxyl-3-methyl coenzyme A (HMG-CoA) reductase, which catalyzes the rate limiting step in cholesterol biosynthesis. Statins are widely prescribed to lower cholesterol in hyperlipidemic patients at risk of cardiovascular disease. More recently, it has been recognized that the protective effects of these drugs extends to myocardial infarction patients with average cholesterol levels. In normocholesterolemic animals, statin therapy has been shown to protect against stroke, ischemia-reperfusion injury of the heart and vascular inflammatory responses, through mechanisms that may be mediated by an increase in endothelium-derived NO production. Endothelium-derived NO is the primary relaxing factor of the large blood vessels and its production is impaired in atherogenic vessels and following ischemia-reperfusion injury. Statin therapy in patient populations has been found to rapidly improve vasomotor response to endothelium-dependent agonists and enhance coronary blood flow. Collectively, these data suggest that statins can act to improve endothelial function through NO-dependent mechanisms that may operate independently of their lipid-lowering action.

The protein kinase Akt serves as a multifunctional regulator of cell survival, growth and glucose metabolism. With respect to its cardiovascular function, Akt acts downstream of the angiogenic growth factors VEGF and angiopoietin to confer endothelial cell survival and ensure proper blood vessel development. Constitutive activation of Akt signaling also protects cardiomyocytes from apoptosis following ischemia-reperfusion injury in vivo. In addition to this cytoprotective role, Akt functions as an activator of endothelial cell NO production in response to VEGF and shear flow through its ability to phosphorylate eNOS on serine 1179. Akt is also essential for directed endothelial cell migration toward VEGF. The ability of Akt to mediate VEGF-induced endothelial cell survival, NO production and migration, suggests that Akt signaling may control the response of the endothelium to angiogenic stimuli.

Figure 1B:
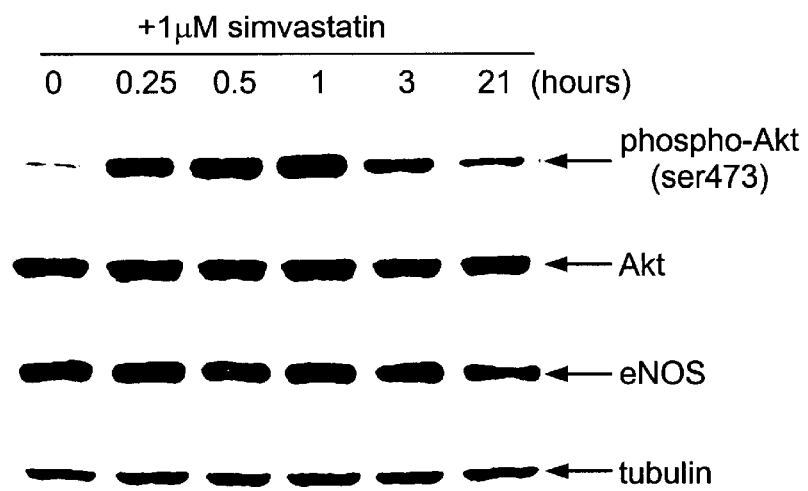
Figure 1C:
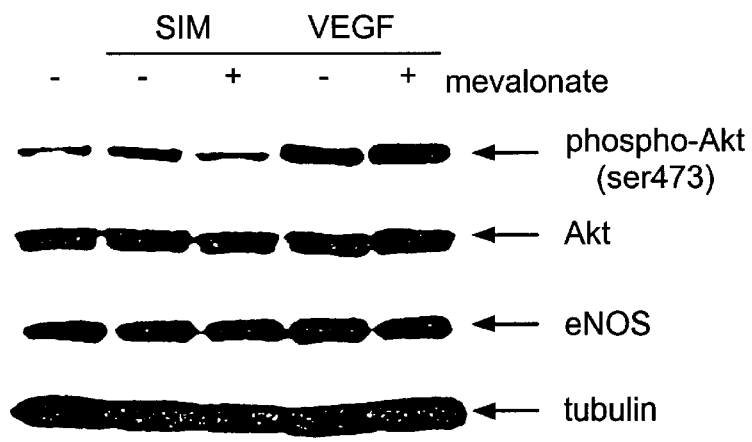
Figure 1D:
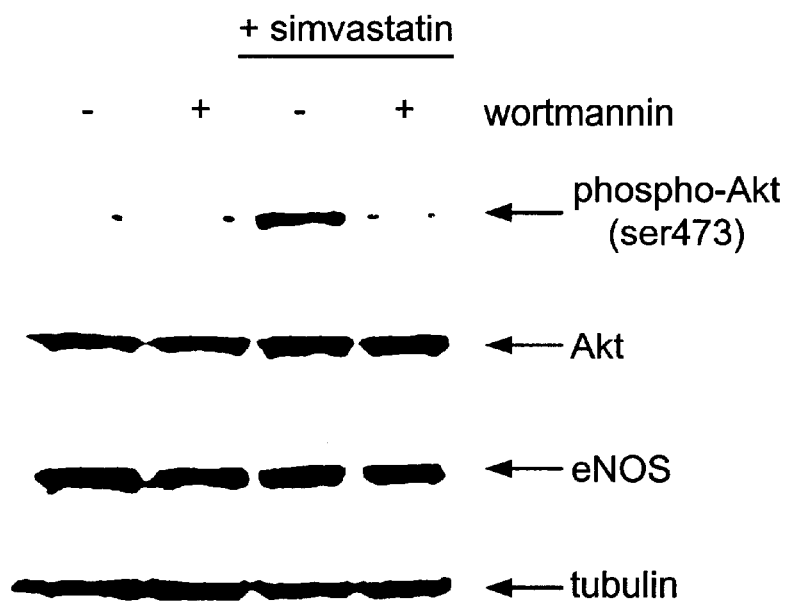
Figure 1E:
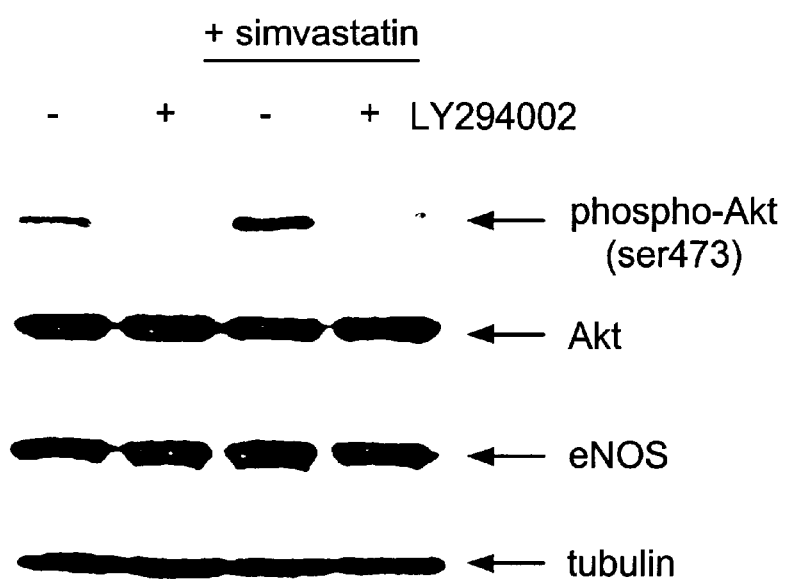

To test whether the beneficial actions of statins on the endothelium are mediated by the Akt signaling pathway, cultured human umbilical vein endothelial cells (HUVEC) were incubated with simvastatin and Akt phosphorylation was assessed at amino acid residue 473 (serine). Simvastatin-treatment led to a dose-dependent increase in serine 473 phosphorylation within 30 minutes, with maximal Akt phosphorylation occurring at 1.0 $\mu$M simvastatin (FIG. 1a). Statin treatment did not affect Akt polypeptide levels, nor did it affect the level of the Akt substrate eNOS. Increased Akt phosphorylation was detected as early as 15 minutes following exposure to 1.0 $\mu$M simvastatin and peaked at approximately 1 hour (FIG. 1b). The level of Akt phosphorylation declined by 3 hours and was further reduced at 21 hours, but remained elevated relative to non-stimulated HUVEC. No changes in total Akt or eNOS protein levels were detected over this time course. Treatment with L-mevalonate, the product of the HMG-CoA reductase reaction, blocked activation of Akt phosphorylation by simvastatin (FIG. 1c). However, mevalonate had no effect on the robust activation of Akt phosphorylation by 100 ng/ml VEGF. Simvastatin-activation of Akt phosphorylation was also blocked by incubation with the phosphoinositide 3-kinase (PI 3-kinase) inhibitors wortmannin (FIG. 1d) and LY294002 (FIG. 1e). Like statin- and mevalonate-treatment, wortmannin and LY294002 had no effect on total Akt or eNOS protein levels (FIGS. 1c, d, e).

To examine the effect of simvastatin on Akt polypeptide kinase activity in HUVEC cultures, lysates prepared from treated cells were immunoprecipitated with anti-Akt antibody and assessed for their ability to phosphorylate histone H2B (FIG. 2a). Akt polypeptide kinase activity was increased in lysates of HUVEC treated with 1.0 $\mu$M simvastatin or 100 ng/ml VEGF. The specificity of the kinase assay was demonstrated by transducing HUVEC cultures with an adenoviral vector encoding a dominant-negative form of Akt, which blocked the increases in kinase activity. Activation of Akt kinase activity was also observed when lysates prepared from simvastatin-treated cells were tested for their ability to phosphorylate a peptide containing the Akt phosphorylation site of eNOS (amino acids 1174 to 1194) (FIG. 2b). Treatment of cells with wortmannin abolished both simvastatin- and VEGF-induced kinase activities toward the eNOS peptide. In contrast, a peptide with alanine substituted for serine at position 1179 did not incorporate appreciable phosphate under any condition tested, demonstrating that the simvastatin-activated phosphorylation occurs at the Akt consensus site within the peptide.

Figure 3A:
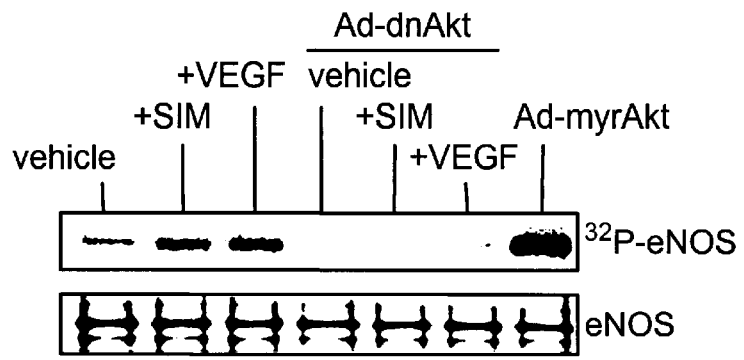
Figure 3B:
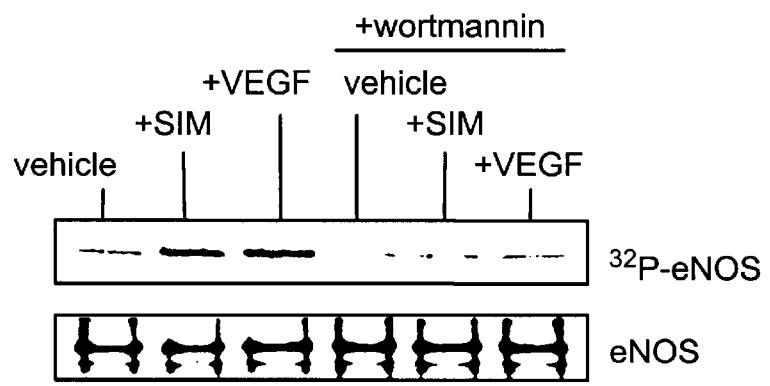

The ability of simvastatin to stimulate Akt-mediated phosphorylation of eNOS in vivo was examined by incubating HUVEC cultures with inorganic $^{32}$P and assessing endogenous eNOS phosphorylation by immunoprecipitation and autoradiography. Treatment with simvastatin or VEGF led to an increase in phosphate incorporation in eNOS, that was blocked when cells were treated with wortmannin or transduced with dominant-negative Akt prior to stimulation (FIGS. 3a, b). In contrast, adenovirus-mediated transduction of constitutively-active Akt (myrAkt) led to the incorporation of phosphate into eNOS in the absence of stimulation with simvastatin or VEGF (FIG. 3a).

Figure 3C:
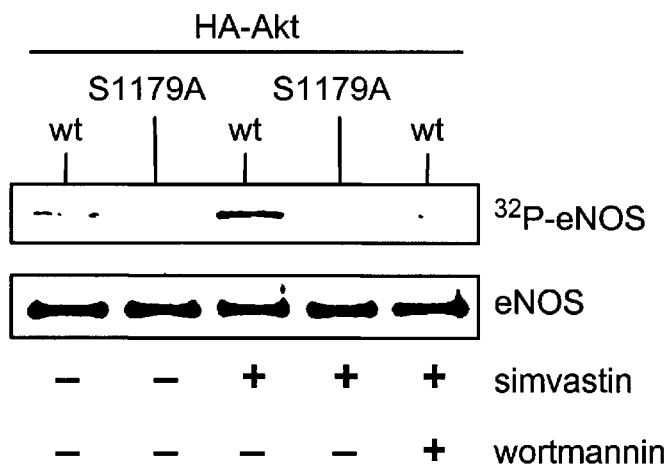

COS cells were transduced with wild-type or mutant eNOS expression plasmids to examine simvastatin-stimulated phosphorylation in greater detail. In this reconstituted system, simvastatin treatment induced phosphate incorporation into wild-type eNOS protein (FIG. 3c). Phosphorylation of eNOS was blocked when cells were treated with wortmannin. Simvastatin-treatment did not induce phosphate incorporation into eNOS when serine 1179 was mutated to an alanine residue, consistent with the in vitro peptide phosphorylation data in FIG. 2b. These data indicate that simvastatin induces phosphate incorporation into eNOS at the Akt phosphorylation site that has been shown to be essential for stimulating catalytic activity in response to VEGF and shear flow. Consistent with this observation, treatment of bovine aortic endothelial cells with simvastatin for 1 hour induced NO release 1.7 fold (from 0.28±0.05 to 0.48±0.07 nmol $NO_2^-$/ml; p<0.05), as determined by NO-specific chemiluminescence (n=4–6). Treatment with wortmannin blocked simvastatin-stimulated NO release (0.26±0.05 nmol $NO_2^-$/ml), but had no affect on basal NO synthesis (0.29±0.07 nmol $NO_2^-$/ml). Under these conditions, there was no detectable change in the level of eNOS protein (FIG. 1 and data not shown), suggesting that simvastatin stimulated eNOS enzymatic activity via phosphorylation of serine 1179.

Akt has been shown to mediate growth factor and anchorage-dependent survival signals in endothelial cells, and NO can function as an autocrine survival signal. Thus, we reasoned that simvastatin might protect endothelial cells from apoptosis through its ability to activate Akt and promote NO synthesis. HUVEC incubated in serum-free media undergo apoptosis as assessed by Annexin-V staining (FIG. 4a). Under these conditions a substantial fraction of the Annexin-V-positive cells are also positive for propidium iodide staining, a marker for later stages of apoptosis. Incubation with simvastatin decreased the number of endothelial cells that were positive for Annexin-V or propidium iodide staining. Apoptosis in HUVEC cultures was also scored by assessing the frequency of pyknotic nuclei observed by staining with Hoechst 33342 (FIG. 4b). Simvastatin promoted endothelial cell survival in a manner similar to VEGF. Incubation with wortmannin or infection with an adenovirus expressing dominant-negative Akt blocked both statin- and VEGF-induced endothelial cell survival. The downstream metabolite mevalonate also blocked the effect of simvastatin on endothelial cell survival. However, mevalonate had no effect on VEGF-induced survival, consistent with its effect on HMG-CoA reductase. In the absence of statin or VEGF stimulation, wortmannin and mevalonate had no detectable effect on survival, whereas infection with Adeno-dnAkt promoted apoptosis slightly (1.2-fold) (data not shown).

We performed tests to determine whether simvastatin could promote revascularization of ischemic tissue. Normocholesterolemic rabbits underwent unilateral resection of their femoral arteries and their major branches, resulting in a marked decrease in hindlimb perfusion. To first demonstrate whether Akt-signaling is sufficient to promote angiogenesis in this model, a method of adenovirus-mediated gene transfer to endothelial cells of the ischemic hindlimb was established (FIG. 5a). Infusion of these limbs with an adenovirus construct expressing β-galactosidase (Adeno-βgal) revealed that transgene expression was restricted to the vascular endothelium (FIG. 5b). Infusion of Adeno-myrAkt in this model enhanced collateral vessel formation (FIG. 5c), and improved tissue perfusion as indicated by an increase in maximal flow in the internal iliac artery at 31 days post-surgery (FIG. 5d). Improved tissue perfusion was also indicated by an increase in calf blood pressure (FIG. 5e). Constitutive Akt signaling in endothelial cells also increased capillary density in the adductor muscle of the ischemic limb (FIG. 5f). In contrast, infusion with Adeno-βgal did not promote vessel formation or tissue perfusion relative to untreated ischemic hindlimbs (control) or vessels infused with saline (FIGS. 5c, d, e, f).

To test the effects of simvastatin on limb revascularization, a dose of 0.1 mg/kg was administered daily by intraperitoneal injection after femoral artery resection. Animals receiving statin treatment displayed more detectable collateral vessels with characteristic corkscrew morphology than the non-treated control group at 40 days following femoral artery resection (FIG. 5c). Correspondingly, the limbs of the simvastatin-treated animals displayed reduced hemodynamic deficit by Doppler flow analysis (simvastatin=46.6±3.0 ml/min; control=32.7±3.3 ml/min; p<0.01; FIG. 5d) and ratio of the systolic pressure of the ischemic limb to that of the normal limb (simvastatin=0.75±0.05; control=0.53±0.04; p<0.01; FIG. 5e). Simvastatin administration also promoted revascularization at the capillary level in the ischemic limb (simvastatin=253±23 capillaries/mm$^2$; control=163±9 capillaries/mm$^2$ in adductor muscle; p<0.01; FIG. 5f). For comparison, some animals received an intramuscular injection of an adenovirus encoding VEGF (Adeno-VEGF) into the thigh of the ischemic limb. Like simvastatin, VEGF treatment enhanced collateral and capillary vessel formation, improved flow and increased calf blood pressure (FIGS. 5c, d, e, f).

These data show that simvastatin rapidly activates Akt polypeptide kinase activity in endothelial cells through a PI 3-kinase-mediated pathway leading to enhanced cellular survival and activation of eNOS. Though the mechanism of Akt activation by simvastatin is not known, inhibition of the HMG-CoA reductase reaction appears to be involved because simvastatin-induced Akt activation was reversed when cultures were incubated with the downstream metabolite mevalonate. In addition to steroid biosynthesis, mevalonate is required for the production of ubiquinone, dolichols and isoprenoids that are essential for diverse cellular processes. It has been reported that statins stabilize eNOS mRNA through changes in isoprenoid synthesis. However, the increase in eNOS transcript levels occur at later time points (24 hours) than is seen with simvastatin activation of eNOS phosphorylation by Akt (15 minutes with no change in eNOS protein level). Of note, the rapid time course of Akt-mediated activation of eNOS by simvastatin is consistent with the acute changes in NO production and vasorelaxation observed in aortic rings following statin treatment ex vivo.

Recent studies have shown that Akt functions downstream of angiogenic growth factors to promote endothelial cell survival, NO synthesis and migration and cellular responses that contribute to the angiogenic process. Here, we provide evidence that enhanced Akt signaling in vascular endothelium promotes revascularization in ischemic tissue. Consistent with this concept, we also demonstrate that statins promote blood vessel formation and improve tissue perfusion on normocholesterolemic animals in a manner similar to treatment with VEGF, suggesting that statin therapy may have utility for stimulating blood vessel growth in patients with severe occlusive vessel disorders. Finally, modulation of Akt activity by this class of drugs may help to explain the improvement in endothelial function, enhanced tissue perfusion and reduction in cardiovascular events that are seen in patients who receive this drug.

Example 1

Methods

Cell Culture, Transfection, and Immunoblot Analysis

Human umbilical endothelial cells (HUVEC) and bovine aortic endothelial cells (BAEC) were cultured in Endothelial Cell Growth Medium (EGM, Clontech). Prior to each experiment, cells were placed in serum-depleted medium (Endothelial Cell Basal Medium, EBM, Clontech) for 4 or 24 hours for HUVEC or 24 hours for BAEC. Experiments were initiated by the addition of the indicated amount of alkaline hydrolysis-activated simvastatin, 100 ng/ml vascular endothelial growth factor (VEGF, R&D Systems) or vehicle. In some experiments, HUVEC were infected with adenoviral constructs encoding dominant-negative or constitutively-active form of Akt1 (dnakt or myrAkt, respectively) at multiplicity of infection (MOI) of 100 for 24 hours in EGM, which results in 95% transduction efficiency. COS-7 cells were plated on 60 mm dish in Dulbecco's minimum essential medium (DMEM) plus 10% fetal bovine serum and transfected with 3 µg of wild type or mutant (S1179A) eNOS expression plasmid and 1 µg of wild type hemagglutinin (HA)-tagged Akt1 expression plasmid using lipofection (Life Technologies). Following transfection and incubation in DMEM without serum for 48 hours, COS-7 cells were stimulated with 1 M simvastatin. In some experiments, cells (HUVEC, BAEC, or COS-7) were pre-treated with wortmannin (500 nM), LY294002 (10 µM) or mevalonate (200 µM) for 1 hour prior to stimulation with simvastatin or VEGF. Mevalonate was activated by alkaline hydrolysis. Cell lysates (30 µg total protein) were resolved by SDS-PAGE (10%), subjected to western immunoblot analysis by using rabbit polyclonal anti-phosphorylated serine 473 residue of Akt1 antibody (New England Biolabs). To verify the amount of loaded proteins, blots were reprobed with goat polyclonal anti-Akt1 antibody (Santa Cruz), mouse monoclonal anti-eNOS antibody (Transduction Laboratories), or mouse monoclonal anti-tubulin antibody (Oncogene). Simvastatin was provided by Merck & Co. (West Point, Pa.) and activated by alkaline hydrolysis.

Akt polypeptide kinase assay.

For assessment of Akt polypeptide kinase activity in vitro, substrate (2 µg histone H2B or 25 µg eNOS peptide) was incubated with Akt immunoprecipitated from cell lysate using goat polyclonal anti-Akt1 antibody (Santa Cruz) as described previously. Kinase reactions were initiated following the addition of reaction components to a final concentration of ATP (50 µM) containing 10 µCi of $^{32}$P-(ATP, DTT (1 mM), HEPES buffer (20 mM, pH 7.4), MnCl$_2$ (10 mM), MgCl$_2$ (10 mM). After incubation for 30 minutes at 30° C., phosphorylated histone H2B was visualized after SDS-PAGE (15%) and autoradiography. To estimate the extent of $^{32}$p incorporation into eNOS peptides, each reaction mixture was measured by spotting onto phosphocellulose disc filter (Amersham-Pharmacia) and the amount of phosphate incorporated and measured by Cerenkov counting. The wild type peptide sequence was 1174-RIRTQSFSLQERHLRGAVPWA-1194, and the mutant eNOS peptide was identical except that serine 1179 was substituted by alanine.

Phosphorylation of eNOS in vivo.

HUVEC or COS-7 cells were placed into phosphate-free DMEM supplemented with 100 µCi/ml of $^{32}$P-orthophosphate for 4 hours prior to stimulation with simvastatin or VEGF. In some samples, cells were infected with adenovirus encoding dominant-negative Akt1 at an MOI of 100 for 24 hours followed by incubation with wortmannin (500 nM) for 1 hour prior to stimulation with simvastatin or VEGF. After 30 minutes stimulation with simvastatin or VEGF, cells were washed with TBS and harvested with lysis buffer (RIPA buffer plus 20 mM NaF, 10 mM $Na_4P_2O_7$, 1 mM $NaVO_4$). The lysate was subjected to immunoprecipitation using mouse monoclonal anti-eNOS antibody (Transduction Laboratories). Radiolabeled phosphate incorporation into each protein was visualized after SDS-PAGE (7.5%) by autoradiography.

Apoptosis Assays

Fluorescence-labeled Annexin-V-FLUOS staining of HUVEC was performed according to manufacturer's instructions (Roche Molecular Biochemicals). Briefly, cells were plated on to chamber slides (Nunc) and placed in EBM for 3 hours. After stimulation for 5 hours with simvastatin, double-staining was performed with Annexin-V-FLUOS (0.1 µg/ml) and propidium iodine (10 µg/ml). For detection of pyknotic nuclei, cells were stained with Hoechst 33342. Where indicated, incubation with wortmannin was initiated 1 hour prior to stimulation with simvastatin or VEGF. Infection with adenovirus encoding dominant-negative Akt1 was initiated 24 hours prior to incubation in EBM media.

NO release from endothelial cells.

Nitric oxide release was measured in the cell supernatant by chemiluminescent detection of nitrate ($NO_2^-$), the stable breakdown product of NO. In brief, BAEC were incubated in EBM for 24 hours following stimulation with simvastatin for 1 hour. In some samples, wortmannin was added 1 hour prior to stimulation. Cell supernatants were collected, deproteinized, and refluxed in glacial acetic acid containing sodium iodide. Processed specimens were measured with a NO analyzer (Sievers).

Limb revascularization studies.

Male New Zealand white rabbits weighing 3.0 to 3.5 kg were utilized to examine the effects of Akt-signaling and simvastatin-mediated stimulation of vessel growth. For the infusion model, the left femoral artery and major side branches were excised from their proximal origin to within 2 cm of the bifurcation into the saphenous and popliteal arteries. After 10 days, to permit postoperative recovery, the distal femoral artery was re-exposed and, after temporary clamping inflow veins, 50 ml of saline, saline with $3.5 \times 10^{10}$ viral particles of Ad-βgal, or saline with $3.5 \times 10^{10}$ viral particles of Ad-myrAkt was infused via the distal femoral artery and incubated for 15 minutes. After clamp removal, the distal femoral artery was ligated. Two animals infused with Adeno-βgal were sacrificed 3 days after surgery to determine β-galactosidase expression in the gastrocnemial muscle. The remainder of the animals (n=6 per experimental group) were analyzed for limb revascularization at 31 days after femoral artery resection. For the intramuscular injection of Adeno-VEGF or the a intraperitoneal injection of simvastatin, the left femoral artery and side branches were completely excised from their proximal origin to the point distally where bifurcation occurs. After 10 days to permit postoperative recovery, a total of $3.5 \times 10^{10}$ viral particles of Adeno-VEGF in 2.5 ml of saline was injected through a 27-gauge needle at a depth of 3 to 5 mm in the adductor (2 sites), medial large (2 sites), and semimembranous (1 site) muscle (500 µl per injection site). Simvastatin was given 0.1 mg/kg/day intraperitoneally until one day before sacrifice. Animals in these groups (n=6 each) were analyzed for limb revascularization 40 days after surgery. Calf blood pressure was measured in both limbs by Doppler flow meter (model 1059, Parks Medical Electronics, Aloha, Oreg.). The calf blood pressure is defined as the ratio of the left calf to right calf systolic pressure. Collateral arteries were evaluated by internal iliac angiography. A 3-F infusion catheter (Tracker-18, Target Therapeutic, San Jose, Calif.) was introduced into the common carotid artery and advanced to the internal iliac artery of the ischemic limb using a 0.014-inch guide wire under fluoroscopic guidance. Nonionic contrast media (Isovue-370, Squibb Diagnostics, New Brunswick, N.J.) was injected at a rate of 1 ml/sec and serial images of the ischemic hindlimb were recorded at a rate of 1 film/sec for 10 seconds. Quantitative angiographic analysis of collateral vessels were performed using a grid overlay composed of 2.5-mm-diameter circles arranged in rows spaced 5 millimeters apart placed over the 4-second angiogram. An angiographic score was calculated as the number of circles crossed by visible arteries divided by the total number of circles in the medial thigh. Intravascular Doppler flow measurements in the internal iliac artery of the ischemic limb were performed with a 0.018-inch Doppler guide wire (Cardiometrics, Inc., Mountain View, Calif.) advanced through a 3F infusion catheter positioned to the internal iliac artery supplying the ischemic limb. Average peak velocity (APV) was recorded after bolus injection of 2 mg papaverine (Sigma Chemical Co.) through the infusion catheter. Angiographic luminal diameter (d) was determined from the angiograms. Doppler flow (ml/min) was calculated as $Q_D = (d^2/4)(0.5 \times APV)$. Capillary density was evaluated using light microscopic sections taken from the adductor muscle of the ischemic limb at the time of euthanasia. Muscle samples were embedded in OCT compound (Miles, Elkhart, Ind.) and snap-frozen in liquid nitrogen. Frozen sections (5 µm in thickness) with muscle fibers oriented in a transverse fashion were stained for alkaline phosphatase using indoxyl-tetrazolium, and then counterstained with 0.5% eosin. The capillary density was calculated as capillaries/$mm^2$ averaged from 10 randomly selected fields.

Statistical analysis.

Data are shown as mean±S.E.M. All data were evaluated with a two tailed, unpaired Student's t test or compared by one-way analysis of variance.

Example 1

References

1. ScandinavianSimvastatinSurvivalStudyGroup. Randomized trial of cholesterol lowering in 4444 patients with coronary heart disease: the Scandinavian Simvastatin Survival Study (4S). *Lancet* 344, 1838–1389 (1994).
2. Levine, G., Keaney Jr., J. & Vita, J. Cholesterol reduction in cardiovascular disease. Clinical benefits and possible mechanisms. *N Engl. J. Med.* 332, 512–521 (1995).
3. Endres, M. et al., Stroke protection by 3-hydroxy-3-methylglutaryl (HMG)-CoA reductase inhibitors mediated by endothelial nitric oxide synthase. *Proc. Natl. Acad. Sci USA* 95, 8880–8885 (1998).
4. Lefer, A. et al., Simvastatin preserves the ischemic-reperfused myocardium in normocholesterolemic rat hearts. *Circulation* 100, 178–184 (1999).
5. Pruefer, D., Scalia, R. & Lefer, A. Simvastatin inhibits leukocyte-endothelial cell interactions and protects against inflammatory processes in normocholesterolemic rats. *Arterioscler. Thromb. Vasc. Biol.* 19, 2894–2900 (1999).
6. Fulton, D. et al., Regulation of endothelium-derived nitric oxide production by protein kinase Akt. *Nature* 399, 597–601 (1999).
7. Gerber, H-P, et al., Vascular endothelial growth factor regulates endothelial cell survival through the phosphatidylinositol 3'-kinase/Akt signal transduction pathway: Requirement for Flk-1/KDR activation. *J. Biol. Chem.* 273, 30336–30343 (1998).

8. Fujio, Y. & Walsh, K., Akt mediates cytoprotection of endothelial cells by vascular endothelial growth factor in an anchorage-dependent manner. *J. Biol. Chem.* 274, 16349–16354 (1999).
9. Goldstein, J. & Brown, M., Regulation of the mevalonate pathway. *Nature* 343, 425–430 (1990).
10. Sacks, F. et al., The effect of pravastatin on coronary events after myocardial infarction in patients with average cholesterol levels. Cholesterol and Recurrent Events Trial investigators. *N. Engl. J. Med.* 335, 1001–1009 (1996).
11. Osborne, J., Siegman, M., Sedar, A., Mooers, S. & Lefer, A., Lack of endothelium-dependent relaxation in coronary resistance arteries of cholesterol-fed rabbits. *Am. J. Physiol.* 256(3 Pt 1), C591–C597 (1989).
12. Lefer, A. & Lefer, D., The role of nitric oxide and cell adhesion molecules on the microcirculation in ischaemia-reperfusion. *Cardiovasc. Res.* 32, 743–751 (1996).
13. Dupuis, J., Tardif, J. -C., Cernacek, P. & Theroux, P., Cholesterol reduction rapidly improves endothelial function after acute coronary syndromes: the RECIFE (Reduction of Cholesterol in Ischemia and Function of the Endothelium) trial. *Circulation* 99, 3227–3233 (1999).
14. Baller, D. et al., Improvement in coronary flow reserve determined by positron emission tomography after 6 months of cholesterol-lowering therapy in patients with early 25 stages of coronary atherosclerosis. *Circulation* 99, 2871–2875 (1999).
15. Datta, S., Brunet, A. & Greenberg, M., Cellular survival: a play in three Akts. *Genes Dev.* 13, 2905–2927 (1999).
16. Kim, I. et al., Angiopoietin-1 regulates endothelial cell survival through the phosphatidylinositol 3'-kinase/Akt signal transduction pathway. *Circ. Res.* 86, 24–29 (2000).
17. Kontos, C. et al., Tyrosine 1101 of Tie2 is the major site of association of p85 and is required for activation of phosphatidylinositol 3-kinase and Akt. *Mol. Cell. Biol.* 18, 4131–4140 (1998).
18. Carmeliet, P. et al., Targeted deficiency or cystosolic truncation of the VE-cadherin gene in mice impairs VEGF-mediated endothelial survival and angiogenesis. *Cell*, 98, 147–157(1999).
19. Fujio, Y., Nguyen, T., Wencker, D., Kitsis, R. & Walsh, K., Akt promotes survival of cardiomyocytes in vitro and protects against ischemia-reperfusion injury in mouse heart. *Circulation* 101, 660–667 (2000).
20. Dimmeler, S. et al., Activation of nitric oxide synthase in endothelial cells by Akt-dependent phosphorylation. *Nature* 399, 601–605 (1999).
21. Morales-Ruiz, M. et al., Vascular endothelial growth factor stimulated actin reorganization and migration of endothelial cells is regulated via the Akt/nitric oxide synthase pathway. *Circ. Res.*, In press. (2000).
22. Dimmeler, S., Haendeler, J., Nehls, M. & Zeiher, A., Suppression of apoptosis by nitric oxide via inhibition of interleukin-1β-converting enzyme (ICE)-like and cysteine protease protein (CPP)-32-like proteases. *J. Exp. Med.* 185, 601–607 (1997).
23. Benjamin, L. E., Goliganin, D., Itin, A., Pode, D. & Keshet, E., Selective ablation of immature blood vessels in established human tumors follows vascular endothelial growth factor withdrawal. *J. Clin. Invest.* 103, 159–165 (1999).
24. Alon, T. et al., Vascular endothelial growth factor acts as a survival factor for newly formed retinal vessels and has implications for retinopathy of prematurity. *Nat. Med.* 1, 1024–1028 (1995).
25. Ziche, M. et al., Nitric oxide synthase lies downstream from vascular endothelial growth factor-induced but not basic fibroblast growth factor-induced angiogenesis. *J. Clin. Invest.* 99, 2625–2634 (1997).
26. Murohara, T. et al., Nitric oxide synthase modulates angiogenesis in response to tissue ischemia. *J. Clin. Invest.* 101, 2567–2578 (1998).
27. Pu, L. Q. et al., Angiogenic growth factor and revascularization of the ischemic limb: Evaluation in a rabbit model. *J. Surg. Res.* 54, 575–583 (1993).
28. Laufs, U. & Liao, J., Post-transcriptional regulation of endothelial nitric oxide synthase mRNA stability by Rho GTPase. *J. Biol. Chem.* 273, 24266–24271 (1998).
29. Kaesemeyer, W., Caldwell, R., Huang, J. & Caldwell, R., Pravastatin sodium activates endothelial nitric oxide synthase independent of its cholesterol-lowering actions. *J. Amer. Coll. Cardiol.* 33, 234–241 (1999).

The invention will be more fully understood by reference to the following examples. These examples, however, are merely intended to illustrate the embodiments of the invention and are not to be construed to limit the scope of the invention.

All documents, including patents and patent applications, are incorporated in their entirety herein by reference.

What is claimed is:

1. A method for promoting angiogenesis in a tissue of a subject in need thereof, comprising:
administering to the subject, an HMG CoA reductase inhibitor or its lactone form in an amount effective to promote angiogenesis in the tissue,
wherein the subject is not otherwise in need of administration of an HMG CoA reductase inhibitor.

2. The method of claim 1, wherein the subject is nonhyperlipidemic and/or nonhypercholesterolemic.

3. The method of claim 1, wherein the subject has a condition selected from the group consisting of hypertension; diabetic peripheral vascular disease; gangrene; Buerger's syndrome; a wound; ischemia of the muscle, brain, kidney, lung, heart or limb; severe occlusive and/or obstructive vascular disease; peripheral vascular disease; myocardial ischemia; myocardial infarction; coronary artery disease; cerebral vascular disease; and visceral vascular disease.

4. The method of claim 1, wherein the HMG CoA reductase inhibitor is a statin molecule.

5. The method of claim 4, wherein the statin molecule is selected from the group consisting of Lovastatin (Mevacor), Pravastatin (Pravachol), Simvastatin (Zocor), Fluvastatin (Lescol), Atorvastatin (Lipitor), or Cerivastatin (Baycol).

6. The method of claim 1, wherein the HMG CoA reductase inhibitor is administered orally.

7. The method of claim 1, wherein the HMG CoA reductase inhibitor is administered locally to a tissue requiring angiogenesis.

8. The method of claim 7, wherein the HMG CoA reductase inhibitor is a statin molecule.

9. The method of claim 8, wherein the statin molecule is in a lactone form prior to administration.

10. The method of claim 8, wherein the statin is selected from the group consisting of Lovastatin (Mevacor), Pravastatin (Pravachol), Simvastatin (Zocor), Fluvastatin (Lescol), Atorvastatin (Lipitor), or Cerivastatin (Baycol).

11. The method of claim 7, wherein administering comprises inserting a stent containing the HMG CoA reductase inhibitor into the tissue.

12. The method of claim 7, wherein administering comprises administering to the subject a pharmaceutical composition comprises an HMG CoA reductase inhibitor and a pharmaceutically acceptable carrier.

13. The method of claim 12, wherein the pharmaceutical composition is formulated as a salve, gel, film or patch.

14. The method of claim 12, wherein the pharmaceutical composition is suitable for topical application.

15. The method of claim 12, wherein the pharmaceutical composition is a controlled release matrix.

16. The method of claim 15, wherein the pharmaceutical composition is formulated to release the HMG CoA reductase inhibitor substantially continuously for a period of at least one day.

17. The method of claim 12, wherein the pharmaceutical composition further comprises an angiogenic growth factor protein.

18. The method of claim 17, wherein the angiogenic growth factor protein is selected from the group consisting of acidic and basic fibroblast growth factors, vascular endothelial growth factor, epidermal growth factor, transforming growth factor α and β, platelet-derived endothelial cell growth factor, platelet-derived growth factor, tumor necrosis factor α, hepatocyte growth factor and insulin like growth factor.

19. The method of claim 12, wherein the pharmaceutical composition further comprises an Akt protein.

20. The method of claim 19, wherein the Akt protein is selected from the group consisting of Akt-1, Akt-2 and Akt-3.

21. The method of claim 19, wherein the Akt protein comprises a myristoylation sequence.

22. The method according to claim 1, wherein the HMG CoA reductase inhibitor is administered at from about 0.01 to 10 mg/kg/day.

23. A method for treating a subject in need of increased blood flow to a tissue, comprising:
   administering to the tissue an HMG CoA reductase inhibitor in an amount effective to promote angiogenesis.

24. A method for promoting angiogenesis, comprising:
   contacting a cell containing an Akt polypeptide with an HMG CoA reductase inhibitor or its lactone form under conditions wherein the HMG CoA reductase inhibitor activates the Akt polypeptide.

25. The method of claim 24, wherein the cell is contacted with an HMG CoA reductase inhibitor in vivo.

26. The method of claim 24, wherein the Akt polypeptide is activated due to phosphorylation at Ser 473 and/or Thr 308.

27. The method of claim 24, wherein the Akt polypeptide is expressed by an endothelial cell.

28. The method of claim 24, wherein the Akt polypeptide is selected from the group consisting of Akt-1, Akt-2 and Akt-3.

29. The method of claim 24, wherein the Akt polypeptide has SEQ ID NO: 1.

30. The method of claim 24, wherein the HMG CoA reductase inhibitor is a statin molecule.

31. The method of claim 30, wherein the statin molecule is selected from the group consisting of Lovastatin (Mevacor), Pravastatin (Pravachol). Simvastatin (Zocor), Fluvastatin (Lescol), Atorvastatin (Lipitor), or Cerivastatin (Baycol).

* * * * *